(12) United States Patent
Hu et al.

(10) Patent No.: US 7,473,711 B2
(45) Date of Patent: Jan. 6, 2009

(54) ANDROGEN MODULATORS

(75) Inventors: Lain-Yen Hu, Ann Arbor, MI (US);
Huangshu Lei, Waltham, MA (US);
Daniel Y. Du, Milan, MI (US); Bruce A. Lefker, Gales Ferry, CT (US)

(73) Assignee: Pfizer Inc., New York, NY (US)

( * ) Notice: Subject to any disclaimer, the term of this patent is extended or adjusted under 35 U.S.C. 154(b) by 193 days.

(21) Appl. No.: 10/599,719

(22) PCT Filed: Apr. 15, 2005

(86) PCT No.: PCT/IB2005/001044

§ 371 (c)(1),
(2), (4) Date: Oct. 6, 2006

(87) PCT Pub. No.: WO2005/102990

PCT Pub. Date: Nov. 3, 2005

(65) Prior Publication Data

US 2007/0197642 A1 Aug. 23, 2007

Related U.S. Application Data

(60) Provisional application No. 60/564,667, filed on Apr. 22, 2004.

(51) Int. Cl.
*A61K 31/085* (2006.01)
*C07D 255/50* (2006.01)

(52) U.S. Cl. .................. 514/721; 558/303; 558/411; 558/425; 514/715; 514/717; 514/718

(58) Field of Classification Search .................. 558/303, 558/411, 425; 514/715, 717, 718, 721
See application file for complete search history.

(56) References Cited

U.S. PATENT DOCUMENTS

| | | | |
|---|---|---|---|
| 4,029,493 A | 6/1977 | Theissen | |
| 4,234,595 A | 11/1980 | Kreighbaum | |
| 4,263,223 A | 4/1981 | Pauly | |
| 4,536,321 A | 8/1985 | Sugimori | |
| 4,992,433 A | 2/1991 | Stokbroekx et al. | |
| 5,108,652 A | 4/1992 | Eidenshink | |
| 5,316,755 A | 5/1994 | Illig et al. | |
| 5,847,166 A | 12/1998 | Buchwald | |
| 5,910,493 A | 6/1999 | Golbs | |
| 6,011,606 A | 1/2000 | Ohe | |
| 2003/0175445 A1 | 9/2003 | Kirsch et al. | |
| 2003/0229129 A1 | 12/2003 | Kraemer et al. | |
| 2003/0232882 A1 | 12/2003 | Miller et al. | |
| 2005/0182132 A1 | 8/2005 | Hu et al. | |
| 2006/0009427 A1 | 1/2006 | Hu et al. | |
| 2006/0252796 A1 | 11/2006 | Barrett et al. | |
| 2007/0072936 A1 | 3/2007 | Barrett et al. | |
| 2007/0197641 A1 | 8/2007 | Hu et al. | |
| 2007/0207987 A1 | 9/2007 | Barrett et al. | |
| 2008/0064745 A1 | 3/2008 | Lefker et al. | |

FOREIGN PATENT DOCUMENTS

| | | |
|---|---|---|
| DE | 2301541 | 9/1973 |
| DE | 3515633 A | 11/1986 |
| DE | 3825170 A1 | 1/1990 |
| DE | 4017019 A1 | 11/1991 |
| DE | 4217928 A1 | 12/1993 |
| DE | 10126434 A | 12/2002 |
| EP | 0002309 | 12/1982 |
| EP | 0080371 A1 | 6/1983 |
| EP | 15505 4 | 9/1985 |
| EP | 0193303 | 9/1986 |
| EP | 221844 A | 5/1987 |
| EP | 100172 B1 | 8/1987 |
| EP | 269383 A | 6/1988 |
| EP | 412814 A | 2/1991 |
| EP | 419286 A | 3/1991 |
| EP | 488474 A1 | 6/1992 |
| EP | 0601977 A1 | 6/1994 |
| EP | 0609587 A | 8/1994 |
| EP | 0673986 A2 | 3/1995 |
| EP | 654468 A1 | 5/1995 |
| EP | 0684235 A1 | 11/1995 |
| EP | 0579223 | 10/1996 |
| EP | 0790235 A1 | 8/1997 |
| EP | 1070753 A2 | 1/2001 |
| EP | 1123933 A1 | 8/2001 |
| EP | 0707007 B1 | 12/2001 |
| EP | 1325910 A1 | 7/2003 |
| EP | 1348433 A | 10/2003 |
| EP | 1348701 A | 10/2003 |
| GB | 1369696 A | 10/1974 |
| GB | 2278054 A | 11/1994 |

(Continued)

OTHER PUBLICATIONS

Kuwabe, S., et al., "Palladium-Catalized Intramolecular C-O Bond Formation", *J. Am. Chem. Soc.*, vol. 123, pp. 12202-12206 (2001).

(Continued)

*Primary Examiner*—Golam M Shameem
(74) *Attorney, Agent, or Firm*—Gregg C. Benson; J. Michael Dixon

(57) ABSTRACT

The present invention is directed to a class of 4-cyano-phenoxy derivatives of formula I and to their use as androgen receptor modulators. Other aspects of the invention are directed to the use of these compounds to decrease excess sebum secretions and to stimulate hair growth.

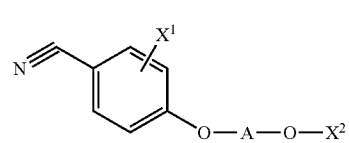

(I)

13 Claims, No Drawings

FOREIGN PATENT DOCUMENTS

| | | |
|---|---|---|
| GB | 2347423 A | 9/2000 |
| JP | 61189243 | 8/1986 |
| JP | 04124183 | 4/1992 |
| JP | 04300877 | 10/1992 |
| JP | 5310616 | 11/1993 |
| JP | 07309850 | 11/1995 |
| JP | 8325154 | 12/1996 |
| JP | 10007647 A | 1/1998 |
| WO | WO9219210 A2 | 7/1992 |
| WO | WO94/05153 A | 3/1994 |
| WO | WO9510521 A1 | 6/1995 |
| WO | WO95/28969 | 11/1995 |
| WO | WO9626921 | 9/1996 |
| WO | WO9735845 A1 | 1/1997 |
| WO | WO98/33779 | 8/1998 |
| WO | WO99/08673 A | 2/1999 |
| WO | WO99/17777 | 4/1999 |
| WO | WO0037430 | 6/2000 |
| WO | WO01/56989 A2 | 8/2001 |
| WO | WO02/06196 | 1/2002 |
| WO | WO02/18333 A | 3/2002 |
| WO | WO0236734 A | 5/2002 |
| WO | WO0241889 A | 5/2002 |
| WO | WO02/057215 A2 | 7/2002 |
| WO | WO02/020484 | 8/2002 |
| WO | WO02060896 A | 8/2002 |
| WO | WO02/085860 A1 | 10/2002 |
| WO | WO02070484 A | 10/2002 |
| WO | WO02/090332 A2 | 11/2002 |
| WO | WO03/004247 | 1/2003 |
| WO | WO03/004269 | 1/2003 |
| WO | WO03/065992 A | 8/2003 |
| WO | WO03066632 A | 8/2003 |
| WO | WO03068217 A | 8/2003 |
| WO | WO03068754 | 8/2003 |
| WO | WO03/074473 A2 | 9/2003 |
| WO | WO03082787 | 10/2003 |
| WO | WO03/093243 A1 | 11/2003 |
| WO | WO2004110994 A1 | 12/2004 |
| WO | WO2005000794 | 1/2005 |
| WO | WO2005/009888 | 2/2005 |
| WO | WO2005013914 A | 2/2005 |
| WO | WO2005042464 A1 | 5/2005 |
| WO | WO2005/049574 A1 | 6/2005 |
| WO | WO2005080320 A1 | 9/2005 |
| WO | WO2005/100305 A1 | 10/2005 |
| WO | WO2005/102990 A1 | 11/2005 |
| WO | WO2005/108361 A1 | 11/2005 |
| WO | WO2006/006065 A1 | 1/2006 |
| WO | WO2006018723 A2 | 2/2006 |
| WO | WO2006018732 A | 2/2006 |
| WO | WO2006/024942 A1 | 3/2006 |
| WO | WO2006/049952 A1 | 5/2006 |

OTHER PUBLICATIONS

Co-pending commonly assigned. U.S. Appl. No. 11/572,760, filed Aug. 8, 2005.

Co-pending commonly assigned. U.S. Appl. No. 11/997,983, filed Jul. 27, 2006.

Abstract: Arnold, Donald R. et al., Radical ions in photochemistry. Part 20. The photochemical nucleophile-olefin combination, aromatic substitution reaction. Canadian Journal of Chemistry (1988) 66 (12), 3012-26.

Gregorio Asensio et al., Synthesis of an enantiopure 2-arylcyclohexanols form prochiral enol acetates by an enantioselective protonation/diastereoselective reduction sequence, Tetrahedron: Asymmetry 14(2003) 3851-3855.

Alexandre Alexakis et al., Enantioselective Nucleophilic Opening fo meso Epoxides by Organolithium Reagents, SYNLETT Oct. 1998, pp. 1165-1167.

Shankar M. Shingh et al., Androgen Receptor Antagonists (Antiandrogens): Structure-Activity Relationships, Current Medicinal Chemistry, 2000, 7, 211-247.

Derwent English Abstract of German Patent Application (DE3939116A1).

Micropatent English Abstract of Japanese Patent (JP2001-247411).

Bohl, Casey E., et al, Structural basis for antagonism and resistance of bicalutamide in prostate cancer, PNAS, Apr. 26, 2005, vol. 102, No. 17 pp. 6201-6206.

Palucki, M. et al., "Palladium-catalyzed intermolecular carbon-oxygen bond formation; A new sysnthesis of aryl ethers".. J. Am. Chem. Soc., 1997, vol. 119, nr. 14, pp. 3395-3396.

Co-pending commonly assigned U.S. Appl. No. 11/053,010, filed Feb. 8, 2005.

Database CA [Online] Chemical Abstracts Service, Columbus, Ohio, US: Yasuda, Kosuke et al: "Preparation of aliphatic nitrogenous five-membered ring compounds as dipeptidyl peptidase IV inhibitors" XP002350473 retrived from STN Database accession No. 136:325560.

Database: CA [Online] Chemical Abstracts Service, Columbus, Ohio, US; Chaki, Hisaaki et al: "Preparation and formulation of alkylsulfonylbiphenyl and aminosulfonylbiphenyl derivatives as selective COX-2 inhibitors" XP002350472 retrieved from STN Database accession No. 125:300608.

Patent Abstracts of Japan vol. 013, No. 021 (C-560), Jan. 18, 1989 & JP 63227502A (SDS Biotech KK), Sep. 21, 1988.

Reiling B A et al: "Effect of prenatal androgenization on performance, lactation, carcass, and sensory traits of heifers in a single-calf heifer system" Journal of Animal Science, vol. 73, No. 4, 1995, pp. 986-992, XP0088065209 ISSN: 0021-8812.

Heitzman R J : "The effectiveness of anabolic agents in increasing rate of growth in farm animals; report on experiments in cattle." Environmental Quality and Safety. Supplement, 1976, No. 5, 1976, pp. 89-98, XP008065222 ISSN: 0340-4714.

Botzki, Salmen: "Structure based design . . . " Cominatorial Science, vol. 24, No. 4, 2005, pp. 458-469, XP008065218.

Loeffler L J et al: "Synthesis of Isosteres of P-Amidinophenylpyruvic Acid Inhibitors of Trypsin, Thrombin, and Pancreatic Kallikrein" Mar. 1, 1975 J. Of Med Chem, Amer. Chem. Soc. Wash. pp. 287-292 XP000574801 ISSN:0022-2623.

Database Caplus Online Chemical Abstracts Service. Columbus. Ohio US Berg. S,S. et al, Chemotherapeutic amidines X. Substituted 4,4'-diamidino-omega.-diphenoxyalkanes and diphenyl ethers XP002333841 retrieved from STN Database accession No. 1949:50548 abstract & Journal of the Chemical Society Abstracts, 1949, pp. 642-648.

Database CAPLUS, Online Chemical Abstracts Service, Columbus, Ohio, US; Kobayashi, Nagao et al: "Optically active phthalocyanines and their circular dichroism" XP002333850 retreived from STN Database accession No. 1993:652129 abstract & Journal of the American Chemical Society, vol. 115, No. 23, 1993, pp. 10994-10995.

Database CAPLUS, Online Chemical Abstracts Service, Columbus, Ohio, US; Keller, Teddy M. et al: "Synthesis of phthalonitriles by nitro displacement" XP002333851 retrieved from STN Database accession No. 1981:442589 abstract & Synthesis, No. 8, 1980, p. 613.

Database CAPLUS, Online Chemical Abstracts Service, Columbus, Ohio, US; Dann, Otto et al: "Syntheses of biscationi, trypanocidal 1-benzofuran compounds" XP002333852 retrieved from STN Database accession No. 1983:53580 abstract & Liebigs Annalen Der Chemie. No. 10, 1982, pp. 1836.

Co-pending commonly assigned, U.S. Appl. No. 11/572,760, filed Aug. 8, 2005.

Co-pending commonly assigned, U.S. Appl. No. 11/572,743, filed Aug. 5, 2005.

Co-pending commonly assigned, U.S. Appl. No. 11/599,143, filed Apr. 1, 2005.

Co-pending commonly assigned, U.S. Appl. No. 60/706,413, filed Aug. 5, 2005.

Co-pending commonly assigned, U.S. Appl. No. 11/572,748, filed Aug. 22, 2005.

ANDROGEN MODULATORS

CROSS REFERENCE TO RELATED APPLICATION

This application is a submission under 35 U.S.C. 371 of PCT/IB2005/0001044 filed on Apr. 15, 2005, which claims priority to U.S. Provisional Application No. 60/564,667, filed on Apr. 22, 2004.

FIELD OF THE INVENTION

The present invention is directed to a new class of 4-cyano-phenoxy derivatives and to their use as androgen receptor modulators. Other aspects of the invention are directed to the use of these compounds to decrease sebum secretion and to stimulate hair growth.

BACKGROUND OF THE INVENTION

Alopecia, or balding, is a common problem which medical science has yet to alleviate. While androgens are associated with balding, the physiological mechanism by which this hair loss occurs is not known. However, it is known that hair growth is altered in individuals afflicted with alopecia.

Hair does not grow continuously but undergoes cycles of activity involving periods of growth, rest, and shedding. The human scalp typically contains from 100,000 to 350,000 hair fibers or shafts, which undergo metamorphosis in three distinct stages:

(a) during the growth phase (anagen) the follicle (i.e. the hair root) penetrates deep into the dermis with the cells of the follicle dividing rapidly and differentiating in the process of synthesizing keratin, the predominant component of hair. In non-balding humans, this growth phase lasts from one to five years;

(b) the transitional phase (catagen) is marked by the cessation of mitosis and lasts from two to three weeks; and (c) the resting phase (telogen) in which the hair is retained within the scalp for up to 12 weeks, until it is displaced by new follicular growth from the scalp below.

In humans, this growth cycle is not synchronized. An individual will have thousands of follicles in each of these three phases. However, most of the hair follicles will be in the anagen phase. In healthy young adults, the anagen to telogen ratio can be as high as 9 to 1. In individuals with alopecia, this ratio is reduced to as low as 2:1.

Androgenetic alopecia arises from activation of an inherited sensitivity to circulating androgenic hormones. It is the most common type of alopecia. It affects both men (50%) and women (30%), primarily of Caucasian origin. Gradual changes in the width and length of the hair shaft are experienced over time and with increasing age, prematurely in some. Terminal hair is gradually converted to short, wispy, colorless vellus hair. As a consequence, men in there 20's and women in their 30's and 40's begin to notice their hair becoming finer and shorter. In males, most of the hair loss occurs at the crown of the head. Females experience a thinning over their entire scalp. As discussed above, the anagen to telogen ratio is reduced significantly, resulting in less hair growth.

Minoxidil, a potassium channel opener, promotes hair growth. Minoxidil is available commercially in the United States under the trademark, Rogaine®. While the exact mechanism of action of minoxidil is unknown, its impact on the hair growth cycle is well documented. Minoxidil promotes the growth of the hair follicle and increase the period of time that the hair follicle is in the anagen phase (i.e., increases the anagen to telogen ratio).

While minoxidil promotes hair growth, the cosmetic efficacy of this growth can vary widely. For example, Roenigk reported the results of a clinical trial involving 83 males who used a topical solution of 3% minoxidil for a period of 19 months. Hair growth occurred in 55% of the subjects. However, only 20% of the subjects considered the growth to be cosmetically relevant. (*Clin. Res.*, 33, No. 4, 914A, 1985). Tosti reported cosmetically acceptable re-growth in 18.1% of his subjects. (*Dermatologica*, 173, No. 3, 136-138, 1986). Thus, the need exists in the art for compounds having the ability produce higher rates of cosmetically acceptable hair growth in patients with alopecia.

SUMMARY OF THE INVENTION

In accordance with the present invention, a new class of 4-cyano-phenoxy derivatives have been discovered. These compounds, their salts, solvates, and prodrugs thereof, may be represented by Formula I below:

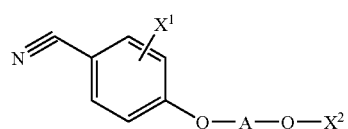

in which;
a) $X^1$ is represented by halogen, cyano, $C_1$-$C_6$ alkoxy, haloalkoxy, or haloalkyl;
b) A is represented by a linear alkylene group containing from 2 to 10 carbon atoms, in which up to 6 hydrogen atoms may optionally be replaced by a substituent independently selected from the group consisting of:
  i) halogen,
  ii) cyano,
  iii) hydroxy,
  iv) ($C_1$-$C_{12}$)alkyl, optionally substituted,
  v) ($C_2$-$C_{12}$)alkenyl, optionally substituted,
  vi) ($C_2$-$C_{12}$)alkynyl, optionally substituted,
  vii) ($C_3$-$C_{10}$)cycloalkyl, optionally substituted,
  viii) ($C_3$-$C_{10}$) cycloalkyl($C_1$-$C_6$)alkyl, in which the alkyl and cycloalkyl moieties may each be optionally substituted,
  ix) $(CH_2)_n$—$SR^1$,
  x) $(CH_2)_n$—O—$R^1$,
  xi) $(CH_2)_n$—$NR^1R^2$,
  xii) $(CH_2)_n$—$COOR^3$ and,
  xiii) $(CH_2)_n$—$CONR^4$;
c) $X^2$ is represented by ($C_6$-$C_{10}$)ary, optionally substituted;
d) n, at each occurrence, is independently represented by an integer from 0 to 6;
e) $R^1$ and $R^2$ are each independently represented by a substituent selected from the group consisting of hydrogen and ($C_1$-$C_6$)alkyl, optionally substituted;
f) $R^3$ is represented by a substituent selected from the group consisting of hydrogen, and ($C_1$-$C_6$)alky, optionally substituted, and;
g) $R^4$ is represented by a substituent selected from the group consisting of hydrogen, and ($C_1$-$C_6$)alky, optionally substituted.

The compounds of Formula I are androgen receptor modulators. The compounds have affinity for the androgen receptor and will cause a biological effect by binding to the receptor. Typically, the compounds will act as antagonists. In selected embodiments they will act as partial agonists, full agonists, or tissue selective agonists. As androgen receptor modulators, the compounds can be used to treat, or alleviate, conditions associated with inappropriate activation of the androgen receptor. Examples of such conditions for antagonists include, but are not limited to, acne, excess sebum secretion, androgenic alopecia, hormone dependant cancers such as prostrate cancer, and hirsutism. Those compounds that are partial agonists, or full agonists, can be used to treat osteoporosis, hypogonadism, anemia, or to stimulate increases in muscle mass, especially in wasting diseases.

The invention is also directed to pharmaceutical compositions containing at least one of the compounds, in an amount effective to modulate activation of the androgen receptor. In a further embodiment, the invention is directed to an article of manufacture containing at least one of the compounds packaged for retail distribution, in association with instructions advising the consumer on how to use the compound to alleviate a condition associated with inappropriate activation of the androgen receptor. An additional embodiment is directed to the use of a compound as a diagnostic agent to detect inappropriate activation of the androgen receptor.

In a further embodiment, the compounds are used topically to induce and/or stimulate hair growth and/or to slow down hair loss. The compounds may also be used topically in the treatment of excess sebum and/or of acne.

DETAILED DESCRIPTION OF THE INVENTION

The headings within this document are only being utilized expedite its review by the reader. They should not be construed as limiting the invention or claims in any manner.

Definitions and Exemplification

As used throughout this application, including the claims, the following terms have the meanings defined below, unless specifically indicated otherwise. The plural and singular should be treated as interchangeable, other than the indication of number:

a. "halogen" refers to a chlorine, fluorine or bromine atom.

b. "$C_1$-$C_6$ alky" refers to a branched or straight chained alkyl group containing from 1 to 6 carbon atoms, such as methyl, ethyl, n-propyl, isopropyl, n-butyl, isobutyl, pentyl, etc.

c. "$C_1$-$C_6$ alkyl, optionally substituted" refers to a branched or straight chained alkyl group containing from 1 to 6 carbon atoms, such as methyl, ethyl, n-propyl, isopropyl, n-butyl, isobutyl, pentyl, etc. Such an alkyl group may be optionally substituted, in which up to 6 hydrogen atoms are replaced by a substituent selected from the group consisting of halogen, haloalkyl, hydroxy, thiol, cyano, and $NR^1R^2$ in which $R^1$ and $R^1$ are as defined above.

d. "$C_1$-$C_{12}$ alkyl, optionally substituted" refers to a branched or straight chained alkyl group containing from 1 to 12 carbon atoms, such as methyl, ethyl, n-propyl, isopropyl, n-butyl, isobutyl, hexyl, octyl, decyl, etc. Such an alkyl group may be optionally substituted, in which up to 8 hydrogen atoms are replaced by a substituent selected from the group consisting of halogen, haloalkyl, hydroxy, thiol, cyano, and —$NR^1R^2$, in which $R^1$ and $R^2$ are as defined above.

e. "$C_2$-$C_{12}$ alkenyl optionally substituted" refers to a straight-chain or branched-chain hydrocarbon radical containing from 2 to 12 carbon atoms and 1, or more, carbon-carbon double bonds. Examples of alkenyl radicals include ethenyl, propenyl, 1,4-butadienyl, 1-hexenyl, 1,3-octadienyl and the like. Such an alkenyl group may be optionally substituted, in which up to 8 hydrogen atoms are replaced by a substituent selected from the group consisting of halogen, haloalkyl, hydroxy, thiol, cyano, and —$NR^1R^2$, in which $R^1$ and $R^2$ are as defined above.

f. "$C_2$-$C_{12}$ alkynyl optionally substituted" refers to a straight-chain or branched-chain hydrocarbon radical containing from 2 to 12 carbon atoms and having 1, or more, carbon-carbon triple bonds. Examples of alkynyl radicals include ethynyl, propynyl, butynyl, octynyl, and the like. Such an alkynyl group may be optionally substituted, in which up to 8 hydrogen atoms are replaced by a substituent selected from the group consisting of halogen, hydroxy, haloalkyl, thiol, cyano, and —$NR^1R^2$, in which $R^1$ and $R^2$ are as defined above.

g. "haloalkyl" refers to a branched or straight chained alkyl group containing from 1 to 6 carbon atoms, in which at least one hydrogen atom is replaced with a halogen (i.e. $C_1$-$C_6$ haloalkyl). Examples of suitable haloalkyl's include chloromethyl, difluoromethyl, trifluoromethyl, 1-fluro-2-chloro-ethyl, 5-fluoro-hexyl, 3-difluro-isopropyl, 3-chloro-isobutyl, etc.

h. "linear alkylene group containing from 2 to 10 carbon atoms" refers to an alky group containing from 2 to 10 carbon atoms serving as a linking group within the molecule (i.e. no terminal —$CH_3$ function). Examples of such alkyl groups include —$CH_2$—$CH_2$—, —$CH_2$—$CH_2$—$CH_2$—, —$CH_2$—$(CH_2)_4$—$CH_2$, —$CH_2$—$(CH_2)_6$—$CH_2$, —$CH_2$—$(CH_2)_8$—$CH_2$—, etc.

i. "($C_1$-$C_2$)alkyl substituted with one or more halogen atoms" refers to a straight chained alkyl group containing 1 or 2 carbon atoms, i.e., methyl or ethyl in which at least one hydrogen atom is replaced with a halogen (i.e. for example trifluromethyl, dichloromethyl, etc.).

j. "($C_1$-$C_2$)alkoxy substituted with one or more halogen atoms" refers to a straight chained alkoxy group containing 1 or 2 carbon atoms, i.e., methoxy or ethoxy in which at least one hydrogen atom is replaced with a halogen ( i.e. for example trifluoromethoxy, difluromethoxy, etc.)

k. "$C_1$-$C_6$ alkoxy" refers to a straight or branched chain alkoxy group containing from 1 to 6 carbon atoms, such as methoxy, ethoxy, n-propoxy, isopropoxy, n-butoxy, isobutoxy, pentoxy, etc.

l. "haloalkoxy" refers to a branched or straight chained alkoxy group containing from 1 to 6 carbon atoms, in which at least one hydrogen atom is replaced with a halogen (i.e. $C_1$-$C_6$ haloalkoxy). Examples of suitable haloalkoxy's include chloromethoxy, difluoromethoxy, trifluoromethoxy, 1-fluro-2-chloro-ethoxy, 5-fluorohexoxy, 3-difluro-isopropoxy, 3-chloro-isobutoxy, etc.

m. "($C_6$-$C_{10}$)aryl" optionally substituted means a cyclic, aromatic hydrocarbon containing from 6 to 10 carbon atoms. Examples of aryl groups include phenyl, naphthyl and biphenyl. Such an aryl moiety may be optionally substituted with up to 4 non-hydrogen substituents, each substituent is independently selected from the group consisting of halogen, cyano, hydroxy, ($C_1$-$C_6$) alkyl, ($C_1$-$C_6$)alkoxy, ($C_1$-$C_2$)alkyl substituted with one or more halogens, ($C_1$-$C_2$)alkoxy substituted with one or more halogens, $SR^5$ and $NR^5R^6$. $R^5$ and $R^6$ are each independently represented by $C_1$-$C_6$ alkyl or hydrogen.

These substituents may be the same or different and may be located at any position of the ring, that is chemically permissible.

n. "$(C_3-C_{10})$ cycloalkyl" optionally substituted refers to a saturated or partially saturated monocyclic, bicyclic or tricyclic alkyl radical wherein each cyclic moiety has 3 to 10 carbon atoms. Examples of cycloalkyl radicals include cyclopropyl, cyclobutyl, cyclopentyl, cyclohexyl, cyclooctyl, and the like. Such a cycloalkyl group may be optionally substituted, in which up to 4 hydrogen atoms are replaced by a substituent selected from the group consisting of halogen, cyano, hydroxy, $(C_1-C_6)$ alkyl, $(C_1-C_6)$alkoxy, $(C_1-C_2)$alkyl substituted with one or more halogens, $(C_1-C_2)$alkoxy substituted with one or more halogens, $SR^5$, and $NR^5R^6$, in which $R^5$ and $R^6$ are as defined above.

o. "androgen" refers to testosterone and its precursors and metabolites, and 5-alpha reduced androgens, including but not limited to dihydrotestosterone. Androgen refers to androgens from the testis, adrenal gland, and ovaries, as well as all forms of natural, synthetic and substituted or modified androgens.

p. "pharmaceutically acceptable" means suitable for use in mammals.

q. "salts" is intended to refer pharmaceutically acceptable salts and to salts suitable for use in industrial processes, such as the preparation of the compound.

r. "pharmaceutically acceptable salts" is intended to refer to either pharmaceutically acceptable acid addition salts" or "pharmaceutically acceptable basic addition salts" depending upon actual structure of the compound.

s. "pharmaceutically acceptable acid addition salts" is intended to apply to any non-toxic organic or inorganic acid addition salt of the base compounds represented by Formula I or any of its intermediates. Illustrative inorganic acids which form suitable salts include hydrochloric, hydrobromic, sulphuric, and phosphoric acid and acid metal salts such as sodium monohydrogen orthophosphate, and potassium hydrogen sulfate. Illustrative organic acids, which form suitable salts include the mono-, di-, and tricarboxylic acids. Illustrative of such acids are for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid, and sulfonic acids such as methane sulfonic acid and 2-hydroxyethane sulfonic acid. Such salts can exist in either a hydrated or substantially anhydrous form. In general, the acid addition salts of these compounds are soluble in water and various hydrophilic organic solvents, and which in comparison to their free base forms, generally demonstrate higher melting points.

t. "pharmaceutically acceptable basic addition salts" is intended to apply to any non-toxic organic or inorganic basic addition salts of the compounds represented by Formula I, or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

u. "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

v. "compound of Formula I", "compounds of the invention", and "compounds" are used interchangeably throughout the application and should be treated as synonyms.

w. "patient" refers to warm blooded animals such as, for example, guinea pigs, mice, rats, gerbils, cats, rabbits, dogs, monkeys, chimpanzees, stump tail macques, and humans.

x. "treat" refers to the ability of the compounds to either relieve, alleviate, or slow the progression of the patient's disease (or condition) or any tissue damage associated with the disease.

Some of the compounds of Formula I will exist as optical isomers. Any reference in this application to one of the compounds represented by Formula I is meant to encompass either a specific optical isomer or a mixture of optical isomers (unless it is expressly excluded). The specific optical isomers can be separated and recovered by techniques known in the art such as chromatography on chiral stationary phases or resolution via chiral salt formation and subsequent separation by selective crystallization. Alternatively, utilization of a specific optical isomer as the starting material will produce the corresponding isomer as the final product.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention. The compounds may also exist in one or more crystalline states, i.e. polymorphs, or they may exist as amorphous solids. All such forms are encompassed by the claims.

All of the compounds of Formula I contain a phenyl ring. To further exemplify the invention, the numbering system for this ring and its substitution pattern is shown below:

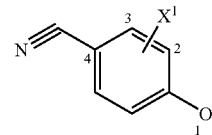

Position 4 of this phenyl ring is substituted with a cyano moiety as depicted above. Position 1 is substituted with an oxygen atom forming an ether moiety. The phenyl ring will be further substituted, as depicted by $X^1$, at position 2 or 3 with a halogen atom, a cyano group, a $(C_1-C_6)$ alkoxy group, a haloalkoxy moiety or a haloalkyl moiety. Typically, it will be a halogen or haloalkyl moiety located at the 3-position. More typically it will be trifluoromethyl located at the 3-position of the phenyl ring.

All of the compounds contain a linear alkylene-linking group as depicted by A. This linking group will contain from 2 to 10 carbon atoms. Typically, it will contain from 2 to 5 carbon atoms, i.e. ethylene, propylene, butylene, or pentylene. More typically, A will be represented by ethylene or propylene. Up to six hydrogen atoms of this alkylene moiety may be replaced by one of the substituents specified above (if chemically permissible). These substituents may be the same, or they may differ. Any single carbon atom of this linear alkylene group may be di-substituted, mono-substituted, or un-substituted.

$X^2$ is represented by a $C_6$-$C_{10}$ aryl moiety, which may optionally be substituted as described above. Typically, this aryl moiety will be a phenyl ring (optionally substituted). In a further embodiment of the invention, $X^2$ is a phenyl ring substituted at the 4-position with a cyano moiety and at the 3-position with a halogen or haloalkyl moiety, typically trifluoromethyl.

More specific embodiments of the invention include compounds of Formula I in which:

$X^1$ is represented by $CF_3$, A is ethylene, propylene, butylene, or pentylene, and $X^2$ is optionally substituted phenyl;

$X^1$ is represented by chloro, A is ethylene, propylene, butylene, or pentylene, and $X^2$ is optionally substituted phenyl;

$X^1$ is represented by $CF_3$, A is ethylene or propylene (mono- or di-substituted with —$CH_3$, or $(CH_2)_n$—O—$R^1$), and $X^2$ is 4-cyano-3-halo-phenyl;

$X^1$ is represented by chloro, A is ethylene or propylene (mono- or di-substituted with —$CH_3$, or $(CH_2)_n$—O—$R^1$), and $X^2$ is 4-cyano-3-halo-phenyl;

$X^1$ is represented by $CF_3$, A is ethylene or propylene (mono- or di-substituted with —$CH_3$, or $(CH_2)_n$—O—$R^1$), and $X^2$ is 4-cyano-3-haloalkyl-phenyl, and;

$X^1$ is represented by chloro, A is ethylene or propylene (mono- or di-substituted with —$CH_3$, or $(CH_2)_n$—O—$R^1$), and $X^2$ is 4-cyano-3-haloalkyl-phenyl.

A further embodiment of the invention are compounds represented by Formula I below, especially those in which A is ethylene or propylene substituted with one or two substituents represented by $C_1$-$C_6$ alkyl, optionally substituted, or —$(CH_2)$n-O—$R^1$, and $X^2$ is as depicted.

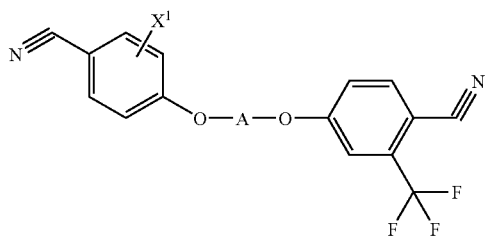

I

More specific examples of compounds represented by formula I include:

a) (1R,2R)-4-[2-(4-cyano-3-trifluoromethyl-phenoxy)-1-methyl-propoxy]-2-trifluoromethyl-benzonitrile (which may also be referred to as 4,4'-[(2S,3S)-butane-2,3-diylbis(oxy)]bis[2-(trifluoromethyl)benzonitrile]);

b) (1S,2S)-4-[2-(4-cyano-3-trifluoromethyl-phenoxy)-1-methyl-propoxy]-2-trifluoromethyl-benzonitrile which may also be referred to as 4,4'-[(2R,3R)-butane-2,3-diylbis(oxy)]bis[2-(trifluoromethyl)benzonitrile];

c) 4-[2-(4-cyano-3-trifluoromethyl-phenoxy)-but-3-enyloxy]-2-trifluoromethyl-benzonitrile which may also be referred to as 4,4'-[but-1-ene-3,4-diylbis(oxy)]bis[2-(trifluoromethyl)benzonitrile];

d) 4,4'-[pentane-1,2-diylbis(oxy)]bis[2-(trifluoromethyl)benzonitrile];

e) 4,4'-[(3-methoxypropane-1,2-diyl)bis(oxy)]bis[2-(trifluoromethyl)benzonitrile];

f) 4,4'-[(3-ethoxypropane-1,2-diyl)bis(oxy)]bis[2-(trifluoromethyl)benzonitrile];

g) 4,4'-[[3-(isopropylamino)propane-1,2-diyl]bis[2-(trifluoromethyl)benzonitrile];

h) 4,4'-[(6-methylhexane-1,2-diyl)bis(oxy)]bis[2-(trifluoromethyl)benzonitrile];

i) 4,4'-[octane-1,2-diylbis(oxy)]bis[2-(trifluoromethyl)benzonitrile];

j) 4-[1-(4-Cyano-3-trifluoromethyl-phenoxymethyl)-2,2-dimethyl-cyclopropoxy]-2-trifluoromethyl-benzonitrile;

k) 4,4'-[propane-1,3-diylbis(oxy)]bis[2-(trifluoromethyl)benzonitrile];

l) 4,4'-[(2-methylpropane-1,3-diyl)bis(oxy)]bis[2-(trifluoromethyl)benzonitrile];

m) 4,4'-[butane-1,3-diylbis(oxy)]bis[2-(trifluoromethyl)benzonitrile];

n) 4-({(3R)-3-[4-cyano-3-(trifluoromethyl)phenoxy]butyl}oxy)-2-(trifluoromethyl)benzonitrile;

o) 4-({(3S)-3-[4-cyano-3-(trifluoromethyl)phenoxy]butyl}oxy)-2-(trifluoromethyl)benzonitrile;

p) 4-{3-[4-cyano-3-(trifluoromethyl)phenoxy]-1,2-dimethylpropoxy}-2-(trifluoromethyl)benzonitrile;

q) 4,4'-[hex-1-ene-4,6-diylbis(oxy)]bis[2-(trifluoromethyl)benzonitrile];

r) 4,4'-[(3-methylbutane-1,3-diyl)bis(oxy)]bis[2-(trifluoromethyl)benzonitrile];

s) 4-{[3-(4-cyanophenoxy)-2-ethylhexyl]oxy}bis[2-(trifluoromethyl)benzonitrile];

t) 4,4'-[(2S,4S)-pentane-2,4-diylbis(oxy)]bis[2-(trifluoromethyl)benzonitrile];

u) 4,4'-[heptane-1,4-diylbis(oxy)]bis[2-(trifluoromethyl)benzonitrile];

v) 4,4'-[hexane-2,5-diylbis(oxy)]bis[2-(trifluoromethyl)benzonitrile];

w) 4,4'-[(2S,5S)-hexane-2,5-diylbis(oxy)]bis[2-(trifluoromethyl)benzonitrile];

x) 4-({5-[4-cyano-2-(trifluoromethyl)phenoxy]pentyl}oxy)-2-(trifluoromethyl)benzonitrile;

y) 4,4'-[hexane-1,5-diylbis(oxy)]bis[2-(trifluoromethyl)benzonitrile];

z) 4,4'-[(3-methylpentane-1,5-diyl)bis(oxy)]bis[2-(trifluoromethyl)benzonitrile];

aa) 4-(1-methoxymethyl-2-phenoxy-ethoxy)-2-trifluoromethyl-benzonitrile;

bb) 4-(1-hydroxymethyl-2-phenoxy-ethoxy)-2-trifluoromethyl-benzonitrile;

cc) (1R)-4-(1-hydroxymethyl-2-phenoxy-ethoxy)-2-trifluoromethyl-benzonitrile;

dd) (1R)-4-(1-methoxymethyl-2-phenoxy-ethoxy)-2-trifluoromethyl-benzonitrile;

ee) (1S)-4-(1-methoxymethyl-2-phenoxy-ethoxy)-2-trifluoromethyl-benzonitrile;

ff) 2-chloro-4-(2-methoxy-1-phenoxymethyl-ethoxy)-benzonitrile;

gg) 2-chloro-4-(1-phenoxymethyl-butoxy)-benzonitrile;

hh) 2-chloro-4-(1-phenoxymethyl-propoxy)-benzonitrile;

ii) 2-chloro-4-(1-phenoxymethyl-butoxy)-benzonitrile;

jj) 2-chloro-4-[1-(4-methoxy-phenoxymethyl-propoxy)-benzonitrile;

kk) 2-chloro-4-[1-(2-methoxy-phenoxymethyl-propoxy)-benzonitrile;

ll) 2-chloro-4-[1-methyl-phenoxy-ethoxy)-benzonitrile;

mm) 4-[4-(4-cyano-3-trifluoromethyl-phenoxy)-2-hydroxy-butyloxy]-2-trifluoromethyl-benzonitrile;

nn) 4-[3-(4-cyano-3-trifluoromethyl-phenoxy)-2-cyclohexyl-propyloxy]-2-trifluoromethyl-benzonitrile;

oo) 4-[3-(4-cyano-3-trifluoromethyl-phenoxy)-2-cyclohexyl-propyloxy]-2-trifluoromethyl-benzonitrile;

pp) 4-[3-(4-cyano-3-trifluoromethyl-phenoxy)-2-chloro-propyloxy]-2-trifluoromethyl-benzonitrile;
qq) 4-[8-(4-cyano-3-trifluoromethyl-phenoxy)-2-chloro-4-hydroxy-octyloxy]-2-trifluoromethyl-benzonitrile;
rr) 4-[10-(4-cyano-3-trifluoromethyl-phenoxy)-2-methyl-cyclopentyl-octyloxy]-2-trifluoromethyl-benzonitrile;
ss) 4-[10-(4-cyano-3-trifluoromethyl-phenoxy)-decy-loxy]-2-trifluoromethyl-benzonitrile;
tt) 4-[7-(4-cyano-3-trifluoromethyl-phenoxy)-2-cyano-4-methyl-6-hydroxy-heptyloxy]-2-trifluoromethyl-benzonitrile;
uu) 4-(3-(3-hydroxy-4-fluoro-phenoxy)-propoxy)-2-trifluoromethyl-benzonitrile;
vv) 4-(2-cyano-4-dimethylamino-8-phenoxy-octyloxy)-2-trifluoromethyl-benzonitrile;
ww) 4-(2-dimethylamino-2-(4-cyano-phenoxy)-ethy-loxy)-2-trifluoromethyl-benzonitrile;
xx) 4-(1-cyclopentyloxymethyl-3-(4-hydroxy-phenoxy)-propoxy)-2-trifluoromethyl-benzonitrile; and
yy) 4-(2-methyl-4-dimethylamino-8-phenoxy-octyloxy)-2-trifluoromethyl-benzonitrile.

Synthesis

The compounds of Formula I can be prepared by methods known in the art. One method for preparing these compounds is described below in Reaction Scheme I.

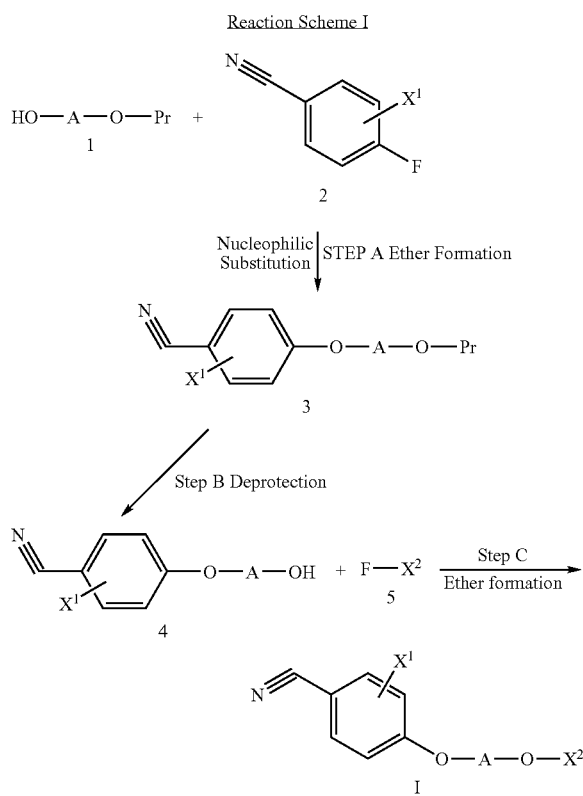

Reaction Scheme I

As depicted above, one of the starting materials is a protected diol as depicted by structure 1, in which A should be represented by the same substituent as required in the final product and Pr represents a suitable protecting group. Examples of suitable protecting groups include methoxymethyl ether(MOM), methoxyethoxymethyl ethers (MEM), ethoxyethyl ethers, trityl ethers, silyl ethers, methyl thiomethyl ethers, benzyl, t-butoxycarbonyl, etc. These diols are known in the art and may be purchased from known commercial sources. Alternatively, they can be prepared as described in J. Am. Chem. Soc. 1993, 115, 4602.

The other starting material is a 4-fluoro-benzonitrile as depicted by structure 2. $X^1$ should be represented by the same moiety as required in the final product. These benzonitriles are known in the art and may be synthesized as described by Japanese Patent Application Number 01097937.

The nucleophilic substitution depicted above may be carried out as is known in the art. The diol of structure 1 is contacted with a slight excess of a base, such as sodium hydride, to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the 4-fluoro-benzonitrile of structure 2 is then added to the reaction medium and the reactants are stirred for a sufficient period of time to allow the alkoxide ion to displace the fluorine from the benzonitrile. This typically takes from 30 minutes to 24 hours. The reaction is typically allowed to warm to room temperature.

The resulting benzonitrile, as depicted by structure 3, can be recovered by extraction, evaporation, or other techniques known in the art. It may then be purified, or used directly in the Deprotection Reaction depicted in Step B.

The deprotection reaction can be carried out as is known in the art, depending upon the particular protecting group used. Typically, the protecting group will be removed with a mild acid, a mild base, or a Lewis acid, depending upon the particular protecting group chosen. The reader's attention is directed to T. W. Greene, *Protective Groups in Organic Synthesis*, John Wiley & Sons, New York, 1991, which provides a description of how to remove commonly used protecting groups. Once the protecting group represented by Pr is removed, the alcohol of structure 4 may be recovered from the reaction by extraction, evaporation, or other techniques known in the art. It may then be purified, or used directly in Step C to produce the desired product of Formula I.

The ether formation depicted in Step C is also a nucleophilic substitution reaction. It may be carried out in the same manner as that described in Step A above. One of the reactants is the alcohol of structure 4, generated via the deprotection reaction of Step B. The other reactant is a fluorinated aryl moiety described by structure 5. $X^2$ should be represented by the same aromatic moiety as required in the final product of Formula I.

The alcohol of structure 4 is contacted with a slight excess of a base, such as sodium hydride, to produce an alkoxide ion. The reaction is carried out in an aprotic solvent, such as tetrahydrofuran, under an inert atmosphere (typically nitrogen) at a temperature of about 0° C. The alcohol is stirred with the base for a period of time ranging from 5 to 60 minutes.

One equivalent of the fluorinated aryl, of structure 5, is then added to the reaction medium and the reactants are stirred for a sufficient period of time to allow the alkoxide ion to displace the fluorine from the aromatic ring. This typically takes from 30 minutes to 24 hours. The reaction is typically allowed to warm to room temperature.

The desired product of Formula I can be recovered by extraction, evaporation, or other techniques known in the art. It may then be optionally purified by chromatography, recrystallization, distillation, or other techniques known in the art.

As is readily apparent to one skilled in the art, the preparation of the compounds of Formula I require the formation of two ether linkages. The particular order in which these ether linkages are formed is not critical. The relevant hydroxyl function is protected and either $X^2$ (structure 5), or the benzonitrile (structure 2), is attached to the diol via the nucleophilic substitution reaction described above, yielding the desired product. Thus, the order in which Step A and Step C are carried out can vary.

As is also readily apparent to those skilled in the art, some of the compounds of Formula I may be prepared in a one step synthesis. Specifically, those compounds of Formula I in which $X^2$ is a benzonitrile (structure 5) having an identical substitution pattern as the benzonitrile (structure 2) attached to the opposite end of the molecule. These compounds may be prepared in a single step as depicted below:

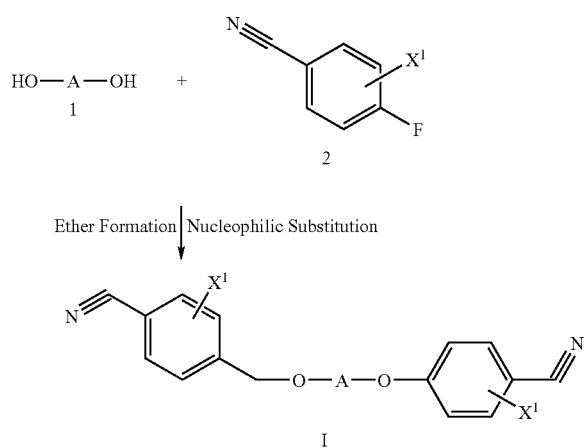

The nucleophilic substitution reaction is carried out in an identical manner to those described above, except that typically two equivalents of the benzonitrile of structure 2 is used. The desired product may then be recovered and purified as described above.

As would be appreciated by those skilled in the art, some of the methods useful for the preparation of such compounds, as discussed above, may require protection of a particular functionality, e.g., to prevent interference by such functionality in reactions at other sites within the molecule or to preserve the integrity of such functionality. The need for, and type of, such protection is readily determined by one skilled in the art, and will vary depending on, for example, the nature of the functionality and the conditions of the selected preparation method. See, e.g., T. W. Greene, *Protective Groups in Organic Synthesis*, John Wiley & Sons, New York, 1991.

Some of the compounds of this invention are acidic and they form a salt with a pharmaceutically acceptable cation. Some of the compounds of this invention are basic and they form a salt with a pharmaceutically acceptable anion. All such salts are within the scope of this invention and they can be prepared by conventional methods such as combining the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. The compounds are obtained in crystalline form according to procedures known in the art, such as by dissolution in an appropriate solvent(s) such as ethanol, hexanes or water/ethanol mixtures.

Medical and Cosmetic Uses

The compounds of Formula I are androgen receptor modulators. They can be used to alleviate conditions associated with inappropriate activation of the androgen receptor. Compounds acting as androgen antagonists may be used to treat, or alleviate, hormone dependent cancers such as prostate carcinomas, benign hyperplasia of the prostate, acne, hirsutism, excess sebum, alopecia, hypertrichosis, precocious puberty, prostamegaly, virilization, and polycystic ovary syndrome. Compounds acting as partial agonists, or full agonists, may be used to treat, or alleviate, male hypogonadism, male sexual dysfunction (impotence, male dysspemtatogenic sterility), abnormal sex differentiation (male hermaphroditism), male delayed puberty, male infertility, aplastic anemia, hemolytic anemia, sickle cell anemia, idiopathic thrombocytopenic purpura, myelofibrosis, renal anemia, wasting diseases (post operative, malignant tumor, trauma, chronic renal disease, burn or AIDS induced), abatement of pain in terminal carcinoma of female genitalia, inoperable breast cancer, mastopathy, endometriosis, female sexual dysfunction, osteoporosis, wound healing and muscle tissue repair.

In order to exhibit the therapeutic properties described above, the compounds need to be administered in a quantity sufficient to modulate activation of the androgen receptor. This amount can vary depending upon the particular disease/condition being treated, the severity of the patient's disease/condition, the patient, the particular compound being administered, the route of administration, and the presence of other underlying disease states within the patient, etc. When administered systemically, the compounds typically exhibit their effect at a dosage range of from about 0.1 mg/kg/day to about 100 mg/kg/day for any of the diseases or conditions listed above. Repetitive daily administration may be desirable and will vary according to the conditions outlined above.

The compounds of the present invention may be administered by a variety of routes. They may be administered orally. The compounds may also be administered parenterally (i.e., subcutaneously, intravenously, intramuscularly, intraperitoneally, or intrathecally), rectally, or topically.

In a typical embodiment, the compounds are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. The dermatological preparation will be applied to the affected area from 1 to 4 times daily. "Dermatologically acceptable" refers to a carrier which may be applied to the skin or hair, and which will allow the drug to diffuse to the site of action. More specifically, it refers the site where inhibition of activation of an androgen receptor is desired.

In a further embodiment, the compounds are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds will most typically be used to alleviate androgenic alopecia, the invention is not limited to this specific condition. The compounds may be used to alleviate any type of alopecia. Examples of non-androgenic alopecia include alopecia areata, alopecia due to radiotherapy or chemotherapy, scarring alopecia, stress related alopecia, etc. As used in this application, "alopecia" refers to partial or complete hair loss on the scalp.

Thus, the compounds can be applied topically to the scalp and hair to prevent, or alleviate balding. Further, the compound can be applied topically in order to induce or promote the growth of hair on the scalp.

In a further embodiment of the invention, a compound of Formula I is applied topically in order to prevent the growth of hair in areas where such hair growth is not desired. One such use will be to alleviate hirsutism. Hirsutism is excessive hair growth in areas that typically do not have hair (i.e. a female face). Such inappropriate hair growth occurs most commonly in women and is frequently seen at menopause. The topical administration of the compounds will alleviate this condition leading to a reduction, or elimination of this inappropriate, or undesired, hair growth.

The compounds may also be used topically to decrease sebum production and more specifically to alleviate oily skin. Likewise the compounds can be used topically to alleviate acne.

In a further embodiment, those compounds acting as partial agonists, or full agonists, may be used to treat, or alleviate, osteoporosis. Osteoporosis is characterized by bone loss, resulting from an imbalance between bone resorption (destruction) and bone formation, which starts in the fourth decade and continues throughout life at the rate of about 1-4% per year (Eastell, Treatment of postmenopausal osteoporosis, *New Eng. J. Med.* 338: 736, 1998). In the United States, there are currently about 20 million people with detectable fractures of the vertebrae due to osteoporosis. In addition, there are about 250,000 hip fractures per year due to osteoporosis, associated with a 12%-20% mortality rate within the first two years, while 30% of patients require nursing home care after the fracture and many never become fully ambulatory again. In postmenopausal women, estrogen deficiency leads to increased bone resorption resulting in bone loss in the vertebrae of around 5% per year, immediately following menopause. Thus, first line treatment/prevention of this condition is inhibition of bone resorption by bisphosphonates, estrogens, selective estrogen receptor modulators (SERMs) and calcitonin. However, inhibitors of bone resorption are not sufficient to restore bone mass for patients who have already lost a significant amount of bone. The increase in spinal BMD attained by bisphosphonate treatment can reach 11% after 7 years of treatment with alendronate. In addition, as the rate of bone turnover differs from site to site; higher in the trabecular bone of the vertebrae than in the cortex of the long bones, the bone resorption inhibitors are less effective in increasing hip BMD and preventing hip fracture. Therefore, osteoanabolic agents, which increase cortical/periosteal bone formation and bone mass of long bones, would address an unmet need in the treatment of osteoporosis especially for patients with high risk of hip fractures.

A number of studies demonstrate that androgens are osteoanabolic in women and men. Anabolic steroids, such as nandrolone decanoate or stanozolol, have been shown to increase bone mass in postmenopausal women. Beneficial effects of androgens on bone in post-menopausal osteoporosis are well documented in recent studies using combined testosterone and estrogen administration (Hofbauer, et al., Androgen effects on bone metabolism: recent progress and controversies, *Eur. J. Endocrinol.* 140, 271-286, 1999). Thus those compounds of Formula I exhibiting agonist or partial agonist activity may be used to treat, or alleviate, osteoporosis, including primary osteoporosis such as senile, postmenopausal and juvenile osteoporosis, as well as secondary osteoporosis, such as osteoporosis due to hyperthyroidism or Cushing syndrome (due to corticosteroid treatment), acromegaly, hypogonadism, dysosteogenesis and hypophosphatasemia. Other bone related indications amendable to treat from androgen agonists include osteoporotic fracture, childhood idiopathic bone loss, alveolar bone loss, mandibular bone loss, bone fracture, osteotomy, periodontitis, or prosthetic ingrowth.

Those compounds acting as agonists, or partial agonists, can also be used to stimulate muscle mass in patients afflicted with wasting diseases, such as AIDS, cancer cachexia, burns, renal disease, etc. Patients suffering from trauma, bedsores, age, etc. can also benefits from the anabolic effects of androgens.

Co-Administration

In a further embodiment of the invention, the compounds of Formula I can be co-administered with other compounds to further enhance their activity, or to minimize potential side effects. For example, potassium channel openers, such as minoxidil, are known to stimulate hair growth and to induce anagen. Examples of other potassium channel openers include (3S,4R)-3,4-dihydro-4-(2,3-dihydro-2-methyl-3-oxopyridazin-6-yl)oxy-3-hydroxy-6-(3-hydroxyphenyl)sulphonyl-2,2,3-trimethyl-2H-benzo[b]pyran, diaxozide, and PO 1075 which is under development by Leo Pharmaceuticals. Such compounds can be co-administered with the compounds of Formula I to alleviate alopecia Thyroid hormone is also known to stimulate hair growth. Synthetic thyroid hormone replacements (i.e., thyromimetics) have also been shown to stimulate hair growth. Such thyromimetics have been described in the literature previously. The reader's attention is directed to European Patent Application No. 1262177, the contents of which are hereby incorporated by reference, for a discussion of such compounds and their use to alleviate alopecia. One particular compound of interest is 2-{4-[3-(4-Fluoro-benzyl)-4-hydroxy-phenoxy]-3,5-dimethyl-phenyl}-2H-[1,2,4]triazine-3,5-dione. Such compounds can be co-administered with the compounds of Formula I to alleviate alopecia.

Anti-androgens can work by a number of different mechanisms. For example, some compounds block the conversion of testosterone to 5-α-dihydrotestosterone, which is responsible for the biological effect in many tissues. 5-Alpha-reductase inhibitors, such as finasteride, have been shown to stimulate hair growth. Finasteride is commercially available from Merck under the trade name Propecia®. Examples of other 5-α-reductase inhibitors include dutasteride (Glaxo Smithkline). Such compounds can be co-administered with the compounds of Formula I to alleviate alopecia.

Protein kinase C inhibitors have also been shown to stimulate hair growth and induce anagen. Calphostin C, which is a selective inhibitor of protein kinase C, has been shown to induce anagen. Other selective protein kinase C inhibitors, such as hexadecylphosphocholine, palmitoyl-DL-carnitine chloride, and polymyxin B sulfate have also been shown to induce anagen. Skin Pharmacol Appl Skin Physiol May-August 2000;13(3-4):133-42. Any such protein kinase C inhibitor can be co-administered with a compound of Formula I to alleviate alopecia.

Immunophilins are a family of cytoplasmic proteins. Their ligands include cyclosporin, FK506, and rapamycin. They are derived from fungi and were developed primarily for their potent immunosuppressive properties. Cyclosporin binds to the proteins, cyclophilins, while FK506 and rapamycin bind to FK binding proteins (FKBPs). All of these compounds have been shown to stimulate hair growth and induce anagen.

Any such immunophilin ligands can be co-administered with a compound of Formula I to alleviate alopecia.

As used in this application, co-administered refers to administering a compound of Formula I with a second anti-alopecia agent, typically having a differing mechanism of action, using a dosing regimen that promotes hair growth in the patient. This can refer to simultaneous dosing, dosing at different times during a single day, or even dosing on different days. The compounds can be administered separately or can be combined into a single formulation. Techniques for preparing such formulations are described below.

Formulations

If desired, the compounds can be administered directly without any carrier. However, to ease administration, they will typically be formulated into pharmaceutical carriers. Likewise, they will most typically be formulated into dermatological, or cosmetic carriers. In this application the terms "dermatological carrier" and "cosmetic" carrier are being used interchangeably. They refer to formulations designed for administration directly to the skin or hair.

Pharmaceutical and cosmetic compositions can be manufactured utilizing techniques known in the art. Typically an effective amount of the compound will be admixed with a pharmaceutically/cosmetically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent, which may also contain suspending agents, sweetening agents, flavoring agents, and preservative agents as are known in the art.

For parenteral administration, the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention will typically be administered topically. As used herein, topical refers to application of the compounds (and optional carrier) directly to the skin and/or hair. The topical composition according to the present invention can be in the form of solutions, lotions, salves, creams, ointments, liposomes, sprays, gels, foams, roller sticks, or any other formulation routinely used in dermatology.

Thus, a further embodiment relates to cosmetic or pharmaceutical compositions, in particular dermatological compositions, which comprise at least one of the compounds corresponding to Formula I above. Such dermatological compositions will contain from 0.001% to 10% w/w % of the compounds in admixture with a dermatologically acceptable carrier, and more typically, from 0.1 to 5 w/w % of the compounds. Such compositions will typically be applied from 1 to 4 times daily. The reader's attention is directed to *Remington's Pharmaceutical Science*, Edition 17, Mack Publishing Co., Easton, Pa. for a discussion of how to prepare such formulations.

The compositions according to the invention can also consist of solid preparations constituting cleansing soaps or bars. These compositions are prepared according to the usual methods.

The compounds can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e. an article of manufacture). Such articles will be labeled and packaged in a manner to instruct the patient how to use the product. Such instructions will include the condition to be treated, duration of treatment, dosing schedule, etc.

The compounds of Formula I may also be admixed with any inert carrier and utilized in laboratory assays in order to determine the concentration of the compounds within the serum, urine, etc., of the patient as is known in the art. The compounds may also be used as a research tool.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention. The following examples and biological data is being presented in order to further illustrate the invention. This disclosure should not be construed as limiting the invention in any manner.

EXAMPLES

Example 1

4,4'-[(2S,3S)-Butane-2,3-diylbis(oxy)]bis[2-(trifluoromethyl)benzonitrile]

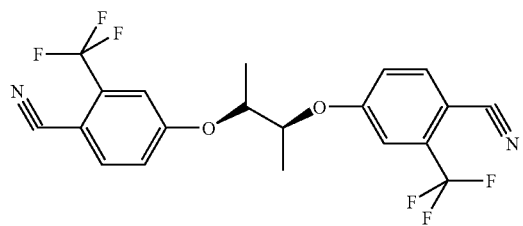

The NaH was suspended in 15 ml of dry THF at 0° C. under $N_2$ gas, then (2R,3R)-2,3-butanediol (0.23 g, 2.46 mmol) was added, this mixture was stirred at 0° C. under $N_2$ for 10 min before adding 4-fluoro-2-(trifluoromethyl)-benzonitrile (1.0 g, 5.18 mmol) The reaction mixture was stirred at 0° C. for 2 hours, then RT(room temperature) for 1 hour. It was quenched with 50 ml of distilled water, extracted with ethyl acetate (3×30 ml), the organic layer was washed with saturated $NaHCO_3$ (three times), the solvent was removed to yield the crude product, it was purified by silica gel column with hexane:ethyl acetate=5:1 as the elute.

MS: 429.0 (M+1 for $C_{20}H_{14}N_2F_6O_2$) LCMS: C-18 Column (25% $H_2O$/75% $CH_3CN$), Ret. Time: 1.36 min Purity: 100%.

Example 2

4,4'-[(2R,3R)-Butane-2,3-diylbis(oxy)]bis[2-(trifluoromethyl)benzonitrile]

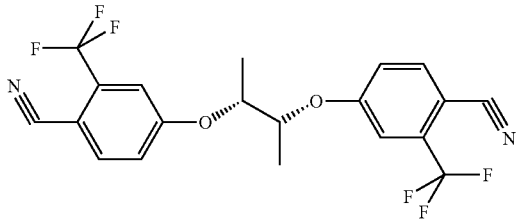

Example 2 was synthesized in accordance with the methods of example 1, except (2S,3S)-2,3-butanediol was used instead of the (2R,3R)-2,3-butanediol. The desired product was purified by column using same conditions as example 1.
MS: 429.0 (M+1 for $C_{20}H_{14}N_2F_6O_2$) LCMS: C-18 Column (25% $H_2O$/75% $CH_3CN$), Ret. Time: 1.38 min Purity: 100%.

Example 3

4,4'-[But-1-ene-3,4-diylbis(oxy)]bis[2-(trifluoromethyl)benzonitrile]

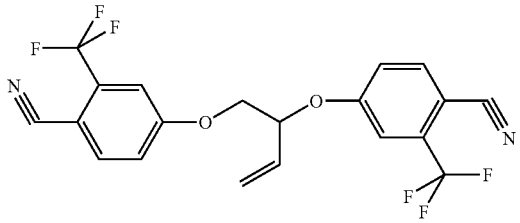

Example 3 was synthesized in accordance with the methods of example 1, except but-3-ene-1,2-diol was used instead of the (2R,3R)-2,3-butanediol. The desired product was purified by column using same conditions as example 1.
MS: 329.2 (M+1 for $C_{16}H_{19}N_2F_3O_2$) LCMS: C-18 Column (50% $H_2O$/50% $CH_3CN$), Ret. Time: 2.65 min Purity: 100%.

Example 4

4,4'-[Pentane-1,2-diylbis(oxy)]bis[2-(trifluoromethyl)benzonitrile]

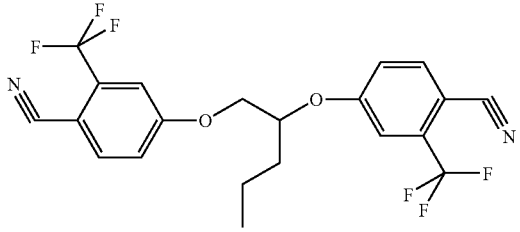

Example 4 was synthesized in accordance with the methods of example 1, except 1,2-pentanediol was used instead of the (2R,3R)-2,3-butanediol. The desired product was purified by column using same conditions as example 1.
MS: 443.1 (M+1 for $C_{21}H_{16}N_2F_6O_2$) LCMS: C-18 Column (25% $H_2O$/75% $CH_3CN$), Ret. Time: 2.25 min Purity: 100%.

Example 5

4,4'-[(3-Methoxypropane-1,2-diyl)bis(oxy)]bis[2-(trifluoromethyl)benzonitrile]

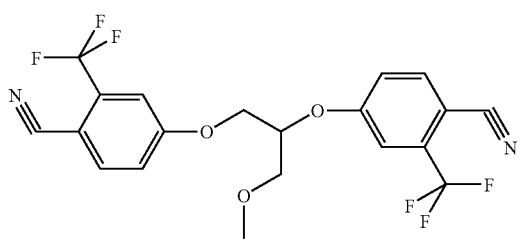

Example 5 was synthesized in accordance with the methods of example 1, except 3-methoxy-1,2-propanediol was used instead of the (2R,3R)-2,3-butanediol. The desired product was purified by column using same conditions as example 1.
MS: 315.1 (M+1 for $C_{15}H_{17}N_2F_3O_2$) LCMS: C-18 Column (50% $H_2O$/50% $CH_3CN$), Ret. Time: 2.31 min Purity: 100%.

Example 6

4,4'-[(3-Ethoxypropane-1,2-diyl)bis(oxy)]bis[2-(trifluoromethyl)benzonitrile]

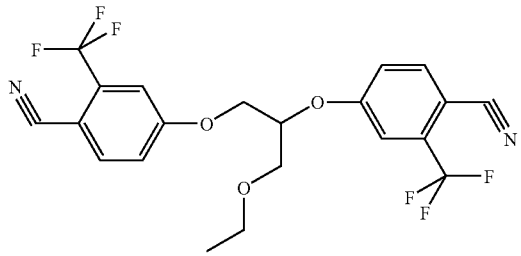

Example 6 was synthesized in accordance with the methods of example 1, except 3-ethoxy-1,2-propanediol was used instead of the (2R,3R)-2,3-butanediol. The desired product was purified by column using same conditions as example 1.
MS: 459.0 (M+1 for $C_{21}H_{16}N_2F_6O_3$) LCMS: C-18 Column (50% $H_2O$/50% $CH_3CN$), Ret. Time: 3.62 min Purity: 99%.

Example 7

4,4'-[[3-(Isopropylamino)propane-1,2-diyl]bis[2-(trifluoromethyl)benzonitrile]

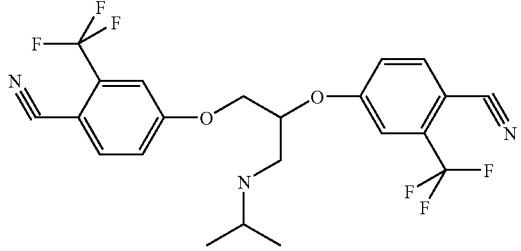

Example 7 was synthesized in accordance with the methods of example 1, except 3-isopropylamino-1,2-propanediol was used instead of the (2R,3R)-2,3-butanediol. The desired product was purified by column using same conditions as example 1
MS: 472.1 (M+1 for $C_{22}H_{19}N_3F_6O_2$) LCMS: C-18 Column (50% $H_2O$/50% $CH_3CN$), Ret. Time: 1.01 min Purity: 100%.

Example 8

4,4'-[(6-Methylhexane-1,2-diyl)bis(oxy)]bis[2-(trifluoromethyl)benzonitrile]

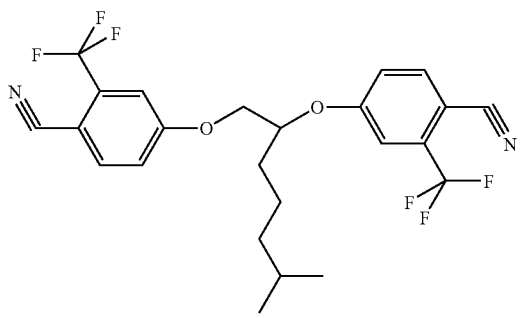

Example 8 was synthesized in accordance with the methods of Example 1, except 6-methyl-1,2-heptanediol was used instead of the (2R,3R)-2,3-butanediol. The desired product was purified by column using same conditions as example 1.
MS: 485.2 (M+1 for $C_{24}H_{22}N_2F_6O_2$) LCMS: C-18 Column (25% $H_2O$/75% $CH_3CN$), Ret. Time: 3.11 min Purity: 100%.

Example 9

4,4'-[Octane-1,2-diylbis(oxy)]bis[2-(trifluoromethyl)benzonitrile]

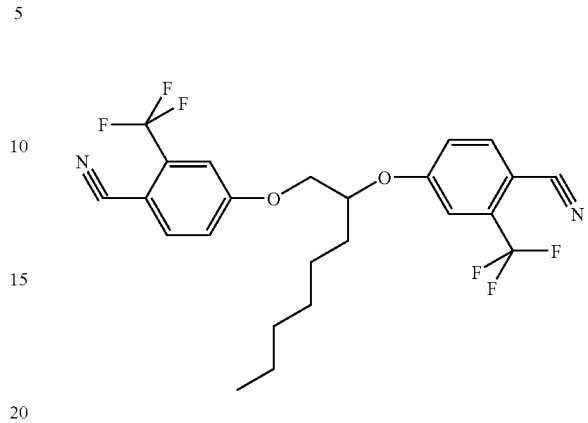

Example 9 was synthesized in accordance with the methods of example 1, except 1,2-octanediol was used instead of the (2R,3R)-2,3-butanediol. The desired product was purified by column using same conditions as example 1.
MS: 485.1 (M+1 for $C_{24}H_{22}N_2F_6O_2$) LCMS: C-18 Column (25% $H_2O$/75% $CH_3CN$), Ret. Time: 3.28 min Purity: 100%.

Example 10

4-[1-(4-Cyano-3-trifluoromethyl-phenoxymethyl)-2,2-dimethyl-cyclopropoxy]-2-trifluoromethyl-benzonitrile

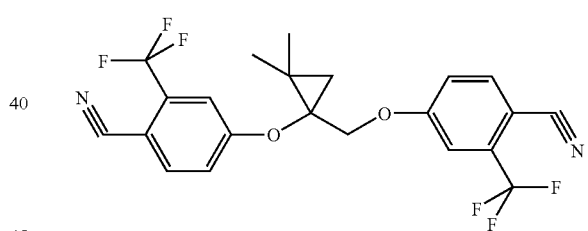

To 1 mL of 0.1M(molar) solutions of the 2-(4-Cyano-3-trifluoromethyl-phenoxy)-4-methyl-pentanoic acid in DMF (dimethylformamide) (0.1 mmol) were added 0.5 mL of a 0.376M solution of HOBT, 1-hydroxybenztriaole, (0.2 mmol) in DMF, 0.1 mL of a 0.1M solution of the C-furan-2-yl-methylamine (0.1 mmol) in DMF, and approximately 183 mg of silica bound carbodiimide (loading: 1.09 g/mmol, 0.2 mmol). The resultant mixtures were shaken and heated at 70° C. for approximately 18 h. The reactions were filtered and the resin thoroughly rinsed with DMF. The solvent was removed in-vacuo to obtain oils that were then purified by HPLC(high performance liquid chromatography).
HPLC conditions:
Column: BHK 30×100 mm ODS-A 5 μm C-18.
Flow rate: 30 mL/min
Solvent: A=Acetonitrile w/3% 1-Propanol; B=Water w/3% 1-Propanol
Method: 0-6.5 min: 15% A, 85% B; 6.5-10.5 min: 100% A
MS: 381.2(M+1 for $C_{19}H_{19}F_3N_2O_3$). LCMS: Atlantis C18 5 cm×4.6 mm, 3 mm column (Solvent: A=Water w/0.1M Formic Acid; B=Acetonitrile w/0.1M Formic Acid, Method: 0-3 min: 90% A, 10% B; 3-5.1 min: 2% A, 98% B; 5.1-7 min: 90% A, 10% B), Ret. Time: 3.64 min. Purity: 85.56%.

Example 11

4,4'-[Propane-1,3-diylbis(oxy)]bis[2-(trifluoromethyl)benzonitrile]

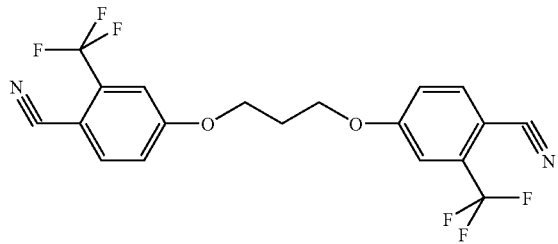

Example 11 was synthesized in accordance with the methods of example 1, except 1,3-propanediol was used instead of the (2R,3R)-2,3-butanediol. The desired product was purified by column using same conditions as example 1.
MS: 415.0 (M+1 for $C_{19}H_{12}N_2F_6O_2$) LCMS: C-18 Column (50% $H_2O$/50% $CH_3CN$), Ret. Time: 3.57 min Purity: 100%.

Example 12

4,4'-[(2-Methylpropane-1,3-diyl)bis(oxy)]bis[2-(trifluoromethyl)benzonitrile]

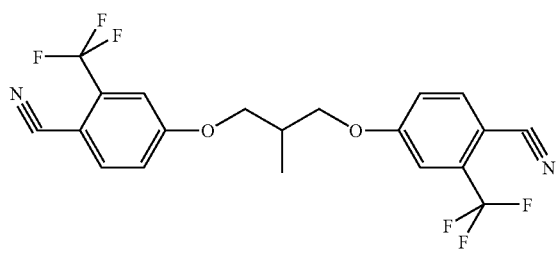

Example 12 was synthesized analogously to Example 1, by substituting the relevant starting materials.
HPLC conditions:
Column: BHK 30×100 mm ODS-A 5 µm C-18.
Flow rate: 30 mL/min
Solvent: A=Acetonitrile w/3% 1-Propanol; B=Water w/3% 1-Propanol
Method: 0-6.5 min: 15% A, 85% B; 6.5-10.5 min: 100% A
MS:411.23(M+1 for $C_{20}H_{21}F_6N_2O$). LCMS: AtlantisC18 5 cm×4.6 mm, 3 mm column (Solvent: A=Water w/0.1M Formic Acid; B=Acetonitrile w/0.1M Formic Acid, Method: 0-3 min: 90% A, 10% B; 3-5.1 min: 2% A, 98% B; 5.1-7 min: 90% A, 10% B), Ret. Time: 3.82 min. Purity: 98.38%.

Example 13

4,4'-[Butane-1,3-diylbis(oxy)]bis[2-(trifluoromethyl)benzonitrile]

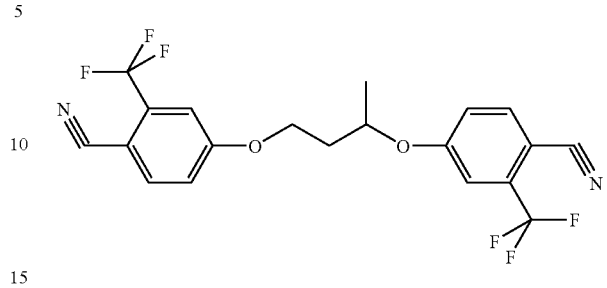

Example 13 was synthesized in accordance with the methods of example 1, except 1,3-butanediol was used instead of the (2R,3R)-2,3-butanediol. The desired product was purified by column using same conditions as example 1.
MS: 429.1 (M+1 for $C_{20}H_{14}N_2F_6O_2$) LCMS: C-18 Column (25% $H_2O$/75% $CH_3CN$), Ret. Time: 2.09 min Purity: 100%.

Example 14

4-({(3R)-3-[4-Cyano-3-(trifluoromethyl)phenoxy]butyl}oxy)-2-(trifluoromethyl)benzonitrile

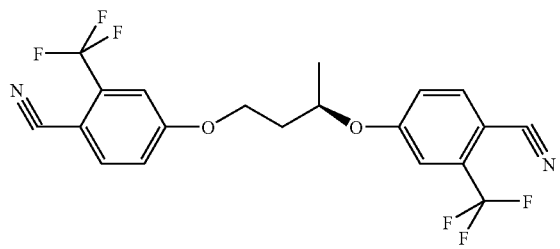

Example 14 was synthesized in accordance with the methods of example 1, except (3R)-1,3-butanediol was used instead of the (2R,3R)-2,3-butanediol. The desired product was purified by column using same conditions as example 1.
MS: 429.1 (M+1 for $C_{20}H_{14}N_2F_6O_2$) LCMS: C-18 Column (25% $H_2O$/75% $CH_3CN$), Ret. Time: 2.01 min Purity: 100%.

Example 15

4-({(3S)-3-[4-Cyano-3-(trifluoromethyl)phenoxy]butyl}oxy)-2-(trifluoromethyl)benzonitrile

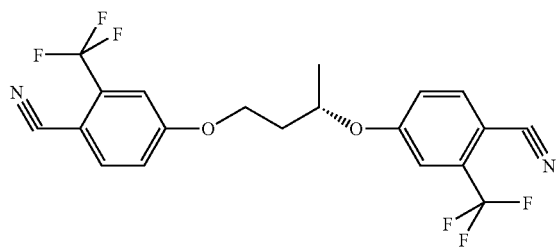

Example 15 was synthesized in accordance with the methods of example 1, except (3S)-1,3-butanediol was used instead of the (2R,3R)-2,3-butanediol. The desired product was purified by column using same conditions as example 1.

MS: 429.1 (M+1 for $C_{20}H_{14}N_2F_6O_2$) LCMS: C-18 Column (25% $H_2O$/75% $CH_3CN$), Ret. Time: 1.81 min Purity: 100%.

Example 16

4-{3-[4-Cyano-3-(trifluoromethyl)phenoxy]-1,2-dimethylpropoxy}-2-(trifluoromethyl)benzonitrile

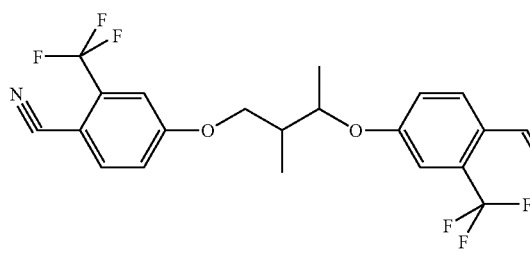

Example 16 was synthesized in accordance with the methods of example 1, except 2-methyl-1,3-butanediol was used instead of the (2R,3R)-2,3-butanediol. The desired product was purified by column using same conditions as example 1.

MS: 443.1 (M+1 for $C_{21}H_{16}N_2F_6O_2$) LCMS: C-18 Column (25% $H_2O$/75% $CH_3CN$), Ret. Time: 1.91 min Purity: 100%.

Example 17

4,4'-[Hex-1-ene-4,6-diylbis(oxy)]bis[2-(trifluoromethyl)benzonitrile]

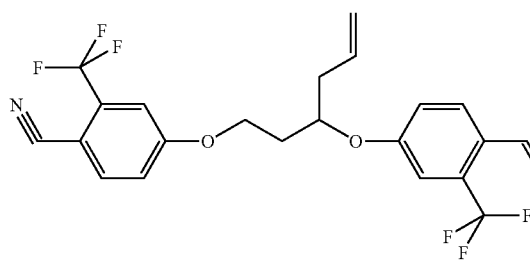

Example 17 was synthesized in accordance with the methods of example 1, except hex-5-ene-1,3-diol was used instead of the (2R,3R)-2,3-butanediol. The desired product was purified by column using same conditions as example 1.

MS: 455.0 (M+1 for $C_{22}H_{16}N_2F_6O_2$) LCMS: C-18 Column (25% $H_2O$/75% $CH_3CN$), Ret. Time: 1.61 min Purity: 100%.

Example 18

4,4'-[(3-Methylbutane-1,3-diyl)bis(oxy)]bis[2-(trifluoromethyl)benzonitrile]

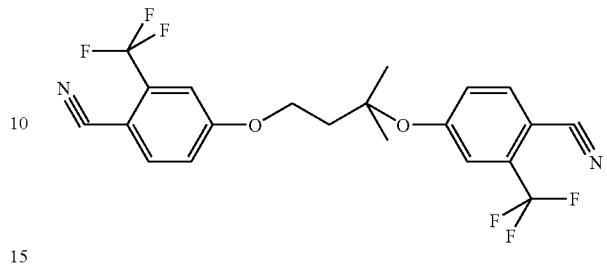

Example 18 was synthesized in accordance with the methods of example 1, except 3-methyl-1,3-butanediol was used instead of the (2R,3R)-2,3-butanediol. The desired product was purified by column using same conditions as example 1.

MS: 443.0 (M+1 for $C_{21}H_{16}N_2F_6O_2$) LCMS: C-18 Column (25% $H_2O$/75% $CH_3CN$), Ret. Time: 3.66 min Purity: 100%.

Example 19

4-{[3-(4-Cyanophenoxy)-2-ethylhexyl]oxy}bis[2-(trifluoromethyl)benzonitrile]

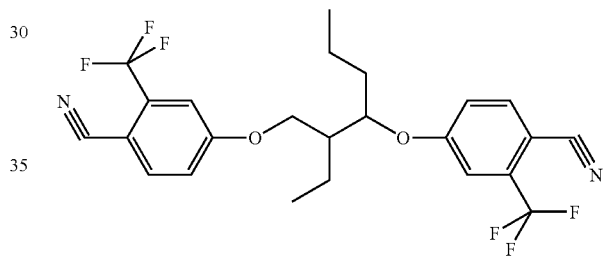

Example 19 was synthesized in accordance with the methods of example 1, except 2-ethyl-hexane-1,3-diol was used instead of the (2R,3R)-2,3-butanediol. The desired product was purified by column using same conditions as example 1.

MS: 485.2 (M+1 for $C_{24}H_{22}N_2F_6O_2$) LCMS: C-18 Column (25% $H_2O$/75% $CH_3CN$), Ret. Time: 1.41 min Purity: 100%.

Example 20

4,4'-[(2S,4S)-Pentane-2,4-diylbis(oxy)]bis[2-(trifluoromethyl)benzonitrile]

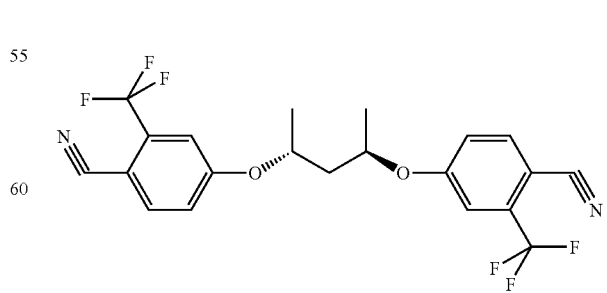

Example 20 was synthesized in accordance with the methods of example 1, except (2R,4S)-pantane-2,4-diol was used instead of the (2R,3R)-2,3-butanediol. The desired product was purified by column using same conditions as example 1.

MS: 443.1 (M+1 for $C_{21}H_{16}N_2F_6O_2$) LCMS: C-18 Column (25% $H_2O$/75% $CH_3CN$), Ret. Time: 1.78 min Purity: 98%.

Example 21

4,4'-[Heptane-1,4-diylbis(oxy)]bis[2-(trifluoromethyl)benzonitrile]

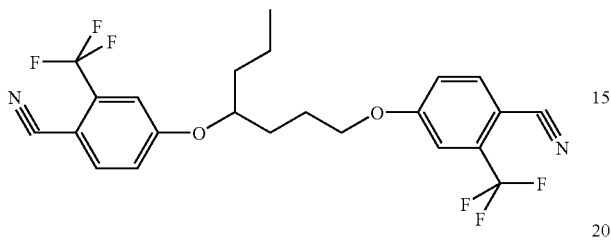

Example 21 was synthesized in accordance with the methods of example 1, except heptane-1,4-diol was used instead of the (2R,3R)-2,3-butanediol. The desired product was purified by column using same conditions as example 1.

MS: 471.1 (M+1 for $C_{23}H_{20}N_2F_6O_2$) LCMS: C-18 Column (25% $H_2O$/75% $CH_3CN$), Ret. Time: 1.48 min Purity: 99%.

Example 22

4,4'-[Hexane-2,5-diylbis(oxy)]bis[2-(trifluoromethyl)benzonitrile]

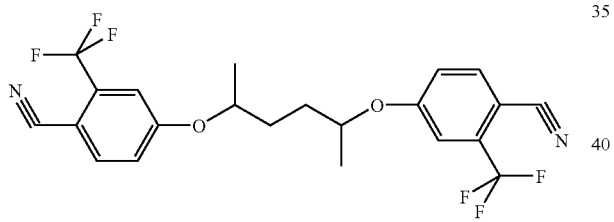

Example 22 was synthesized in accordance with the methods of example 1, except hexane-2,5-diol was used instead of the (2R,3R)-2,3-butanediol. The desired product was purified by column using same conditions as example 1.

MS: 457.1 (M+1 for $C_{22}H_{18}N_2F_6O_2$) LCMS: C-18 Column (25% $H_2O$/75% $CH_3CN$), Ret. Time: 2.14 min Purity: 97%.

Example 23

4,4'-[(2S,5S)-Hexane-2,5-diylbis(oxy)]bis[2-(trifluoromethyl)benzonitrile]

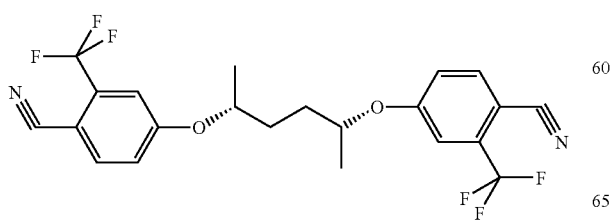

Example 23 was synthesized in accordance with the methods of example 1, except (2S,5S)-hexane-2,5-diol was used instead of the (2R,3R)-2,3-butanediol. The desired product was purified by column using same conditions as example 1.

MS: 457.1 (M+1 for $C_{22}H_{18}N_2F_6O_2$) LCMS: C-18 Column (25% $H_2O$/75% $CH_3CN$), Ret. Time: 2.28 min Purity: 100%.

Example 24

4-({5-[4-Cyano-2-(trifluoromethyl)phenoxy]pentyl}oxy)-2-(trifluoromethyl)benzonitrile

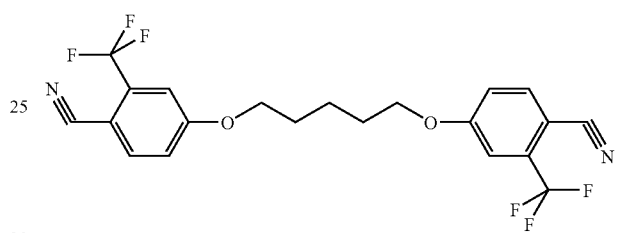

Example 24 was synthesized in accordance with the methods of example 1, except pantane-1,5-diol was used instead of the (2R,3R)-2,3-butanediol. The desired product was purified by column using same conditions as example 1.

MS: 443.1 (M+1 for $C_{21}H_{16}N_2F_6O_2$) LCMS: C-18 Column (25% $H_2O$/75% $CH_3CN$), Ret. Time: 2.02 min Purity: 100%.

Example 25

4,4'-[Hexane-1,5-diylbis(oxy)]bis[2-(trifluoromethyl)benzonitrile]

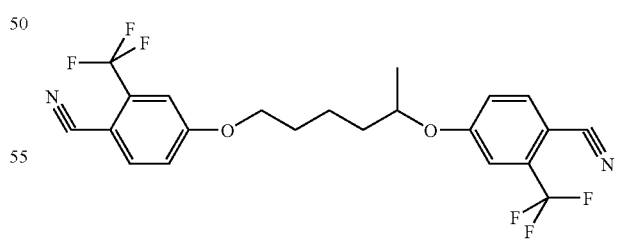

Example 25 was synthesized in accordance with the methods of example 1, except hexane-1,5-diol was used instead of the (2R,3R)-2,3-butanediol. The desired product was purified by column using same conditions as example 1

MS: 457.1 (M+1 for $C_{22}H_{18}N_2F_6O_2$) LCMS: C-18 Column (25% $H_2O$/75% $CH_3CN$), Ret. Time: 2.48 min Purity: 100%.

Example 26

4,4'-[(3-Methylpentane-1,5-diyl)bis(oxy)]bis[2-(trifluoromethyl)benzonitrile]

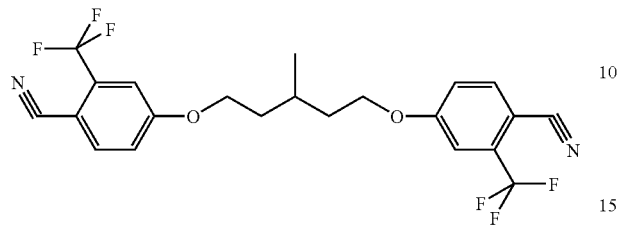

Example 26 was synthesized in accordance with the methods of example 1, except 3-methyl-pantane-1,5-diol was used instead of the (2R,3R)-2,3-butanediol. The desired product was purified by column using same condition as example 1.
MS: 457.1 (M+1 for $C_{22}H_{18}N_2F_6O_2$) LCMS: C-18 Column (25% $H_2O$/75% $CH_3CN$), Ret. Time: 2.52 min Purity: 100%.

Example 27

4-(1-Methoxymethyl-2-phenoxy-ethoxy)-2-trifluoromethyl-benzonitrile

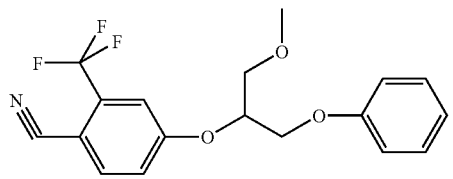

Step 1: Preparation of 1-Methoxy-3-phenoxy-propan-2-ol

2-Phenoxymethyl-oxirane (0.15 g, 1.00 mMol) and sodium methoxide (0.054 g, 1.00 mMol) were dissolved in 10 ml of MeOH, then the reaction mixture was refluxed for 3 hours. The solvent MeOH was removed and the residue was extracted with ethyl acetate (3×20 ml), it was washed with brine, dried over MgSO4. The crude product was purified by column (25% EtOAc/Hexane) to yield 1-methoxy-3-phenoxy-propan-2-ol, whose structure is depicted below:

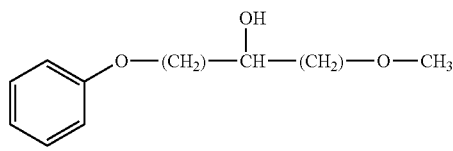

Step 2: Preparation of 4-(1-Methoxymethyl-2-phenoxy-ethoxy)-2-trifluoromethyl-benzonitrile 4-(1-Methoxymethyl-2-phenoxy-ethoxy)-2-trifluoromethyl-benzonitrile was synthesized in accordance with the methods of example 1, except the 1-methoxy-3-phenoxy-propan-2-ol, produced above, was used instead of the (2R, 3R)-2,3-butanediol. The desired product was purified by column using same conditions as example 1.
MS: 352.1 (M+1 for $C_{18}H_{16}NF_3O_3$) LCMS: C-18 Column (50% $H_2O$/50% $CH_3CN$), Ret. Time: 3.37 min Purity: 100%.

Example 28

4-(1-Hydroxymethyl-2-phenoxy-ethoxy)-2-trifluoromethyl-benzonitrile

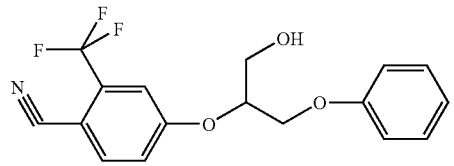

The starting material, 4-(1-methoxymethyl-2-phenoxy-ethoxy)-2-trifluoromethyl-benzonitrile, which is the product of Example 27, (0.5 g, 1.4 mmol) was dissolved in 10 ml of dry $CH_2Cl_2$, it was cooled to −78° C. before addition of $BBr_3$ (4.3 ml of 1.0M solution in $CH_2Cl_2$). After 2 hours, the reaction mixture was gradually warmed up to room temperature; the reaction was quenched with 45 ml of saturated $NaHCO_3$, extracted with $CHCl_3$ (3×20 ml). Purification: Silica Gel
Column: Hexane:ethyl acetate=1:1.
Column: Hexane:ethyl acetate=5:1.
MS: 338.0 (M+1 for $C_{17}H_{14}NF_3O_3$) LCMS: C-18 Column (25% $H_2O$/75% $CH_3CN$), Ret. Time: 1.12 min Purity: 99.5%.

Example 29

(1R)-4-(1-Hydroxymethyl-2-phenoxy-ethoxy)-2-trifluoromethyl-benzonitrile

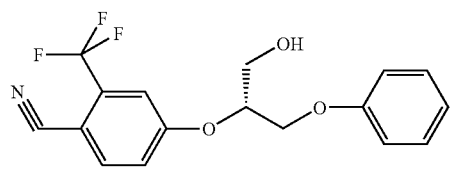

The product of Example 29 was prepared by chiral HPLC separation of the product of Example 28. The desired product was purified by LCMS as described below:
Chiral separation column: chiralpak AD, 20×250 mm.
Solvent: hexane+0.1% TFA.
Run time: 30 min.
MS: 338.0 (M+1 for $C_{17}H_{14}NF_3O_3$) LCMS: C-18 Column (25% $H_2O$/75% $CH_3CN$),
Ret. Time: 1.06 min Purity: 99.0%.
Optical rotation: [a]=+30.4 (EtOH)

Example 30

(1R)-4-(1-Methoxymethyl-2-phenoxy-ethoxy)-2-trifluoromethyl-benzonitrile

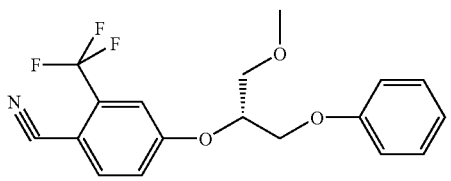

The product of Example 30 was prepared by chiral HPLC separation of the product of Example 27. The desired product was purified by LCMS as described below:
Chiral separation column: chiralpak AD, 20×250 mm.
Solvent: hexane+0.1% TFA.
Run time: 50 min.
MS: 352.1 (M+1 for $C_{18}H_{16}NF_3O_3$) LCMS: C-18 Column (25% $H_2O$/75% $CH_3CN$),
Ret. Time: 1.55 min Purity:100%.
Optical rotation: [a]=+37.5 ($CHCl_3$)

Example 31

(1S)-4-(1-Methoxymethyl-2-phenoxy-ethoxy)-2-trifluoromethyl-benzonitrile

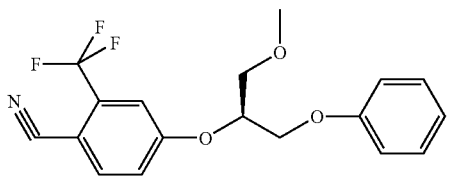

The product of Example 31 was prepared by chiral HPLC separation of the product of Example 27. The desired product was purified by LCMS as described below:
Chiral separation column: chiralpak AD, 20×250 mm.
Solvent: hexane+0.1% TFA.
Run time: 50 min.
MS: 352.1 (M+1 for $C_{18}H_{16}NF_3O_3$) LCMS: C-18 Column (25% $H_2O$/75% $CH_3CN$),
Ret. Time: 1.53 min Purity:100%.
Optical rotation: [a]=−35.1 ($CHCl_3$)

Example 32

The compounds of Formula I have affinity for the androgen receptor. This affinity has been demonstrated for selected compounds using the human receptor. The description below describes how the assay was carried out.

Competitive binding analysis was performed on baculovirus/Sf9 generated hAR extracts in the presence or absence of different concentrations of test agent and a fixed concentration of $^3$H-dihydrotestosterone ($^3$H-DHT) as tracer. This binding assay method is a modification of a protocol previously described (Liao S., et. al. *J. Steroid Biochem.* 20:11-17 1984). Briefly, progressively decreasing concentrations of compounds are incubated in the presence of hAR extract (Chang et al. *P.N.A.S.* Vol. 89, pp. 5546-5950, 1992), hydroxylapatite, and 1 nM $^3$H-DHT for one hour at 4° C. Subsequently, the binding reactions are washed three times to completely remove excess unbound $^3$H-DHT. hAR bound $^3$H-DHT levels are determined in the presence of compounds (i.e. competitive binding) and compared to levels bound when no competitor is present (i.e. maximum binding). Compound binding affinity to the hAR is expressed as the concentration of compound at which one half of the maximum binding is inhibited. Table II below provides the results that were obtained for selected compounds (reported data is the mean of multiple tests as shown below)

TABLE II

| Example # | Structure | AR Binding $IC_{50}$ (nM) |
|---|---|---|
| 1 | 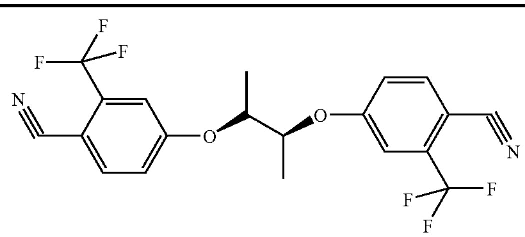 | 191 (c) |
| 2 | 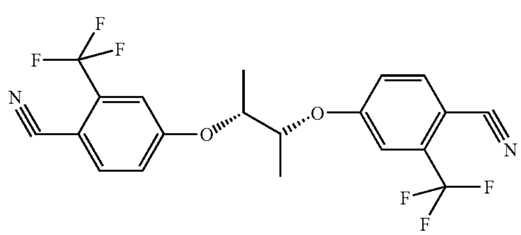 | 34 (c) |

TABLE II-continued

| Example # | Structure | AR Binding IC$_{50}$ (nM) |
|---|---|---|
| 3 | 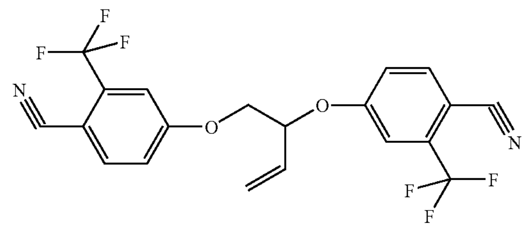 | 115 (a) |
| 4 | 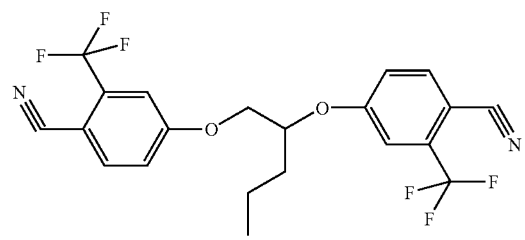 | 630 (b) |
| 5 | 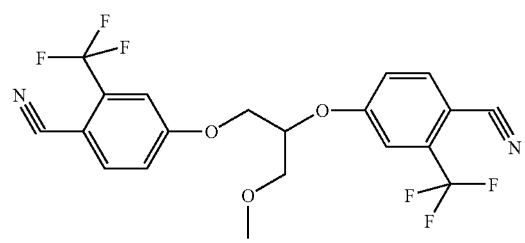 | 56 (a) |
| 6 | 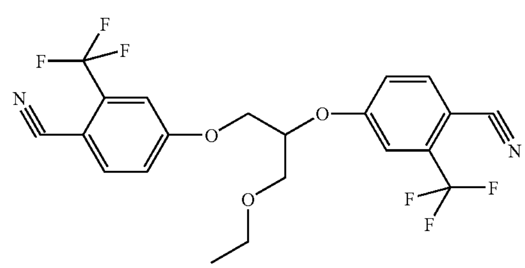 | 124 (a) |
| 7 | 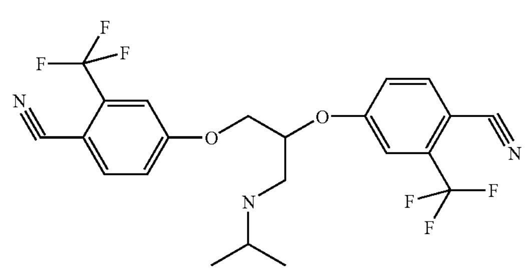 | 319 (a) |

TABLE II-continued
| Example # | Structure | AR Binding IC$_{50}$ (nM) |
|---|---|---|
| 8 | 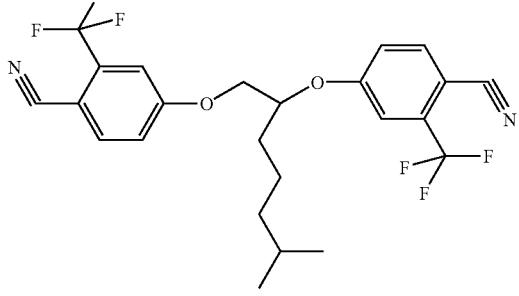 | 967 (a) |
| 9 | 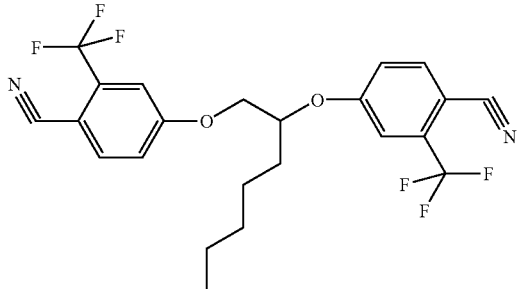 | 109 (a) |
| 10 | 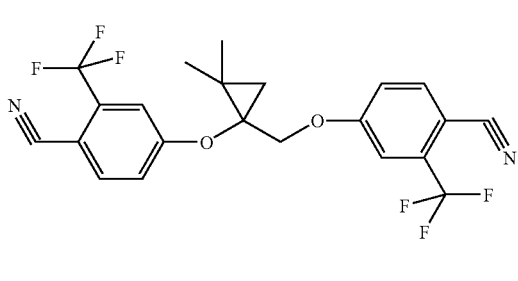 | 174 (a) |
| 11 | 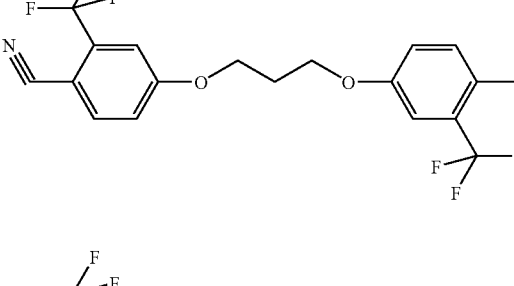 | 165 (c) |
| 12 | 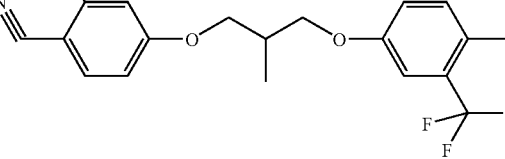 | 233 (c) |

TABLE II-continued

| Example # | Structure | AR Binding IC$_{50}$ (nM) |
|---|---|---|
| 13 | 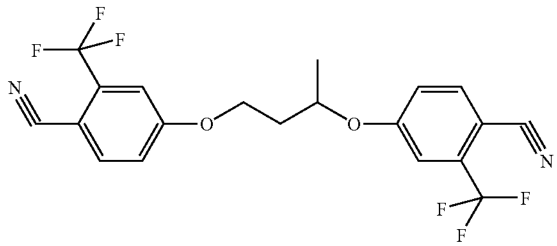 | 10 (a) |
| 14 | 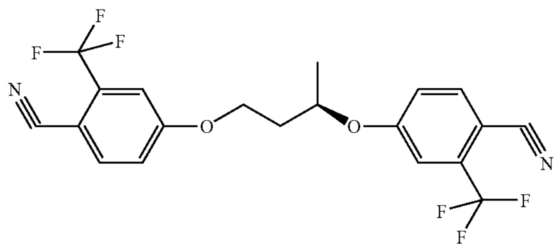 | 281 (a) |
| 15 | 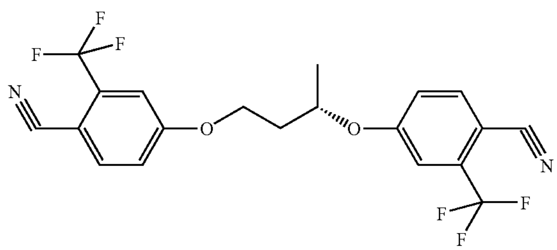 | 49 (a) |
| 16 | 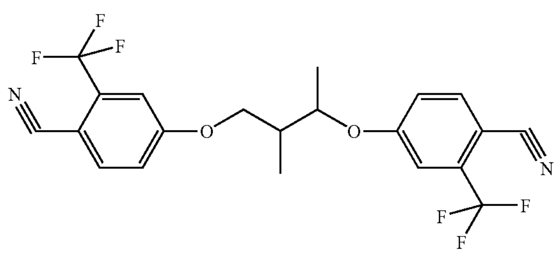 | 372 (a) |
| 17 | 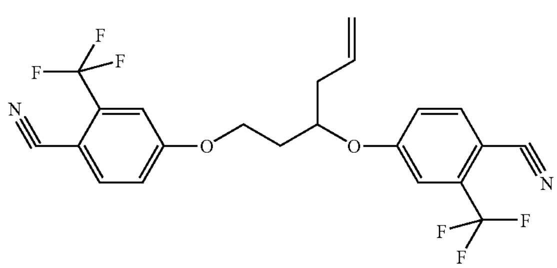 | 47 (a) |
| 18 | 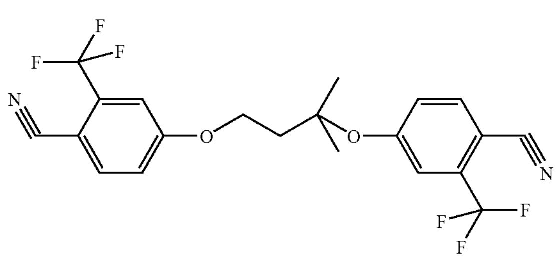 | 410 (a) |

TABLE II-continued

| Example # | Structure | AR Binding IC$_{50}$ (nM) |
|---|---|---|
| 19 | 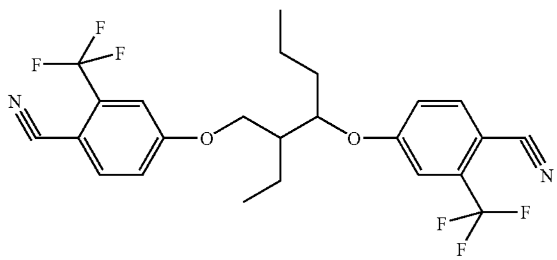 | 216 (b) |
| 20 | 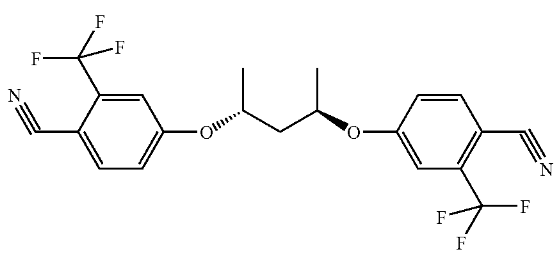 | 17 (a) |
| 21 | 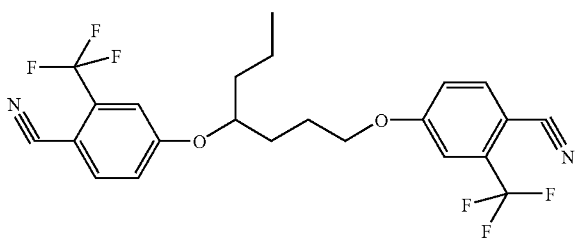 | 233 (a) |
| 22 | 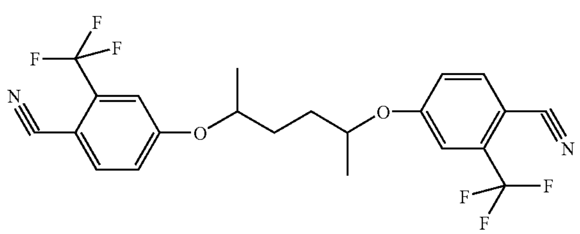 | 293 (a) |
| 23 | 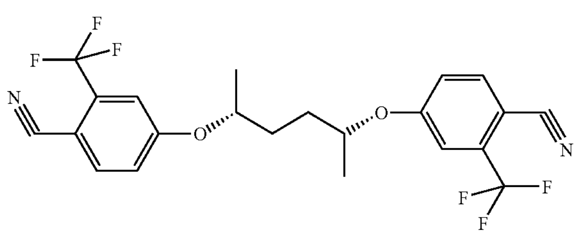 | 180 (a) |
| 24 | 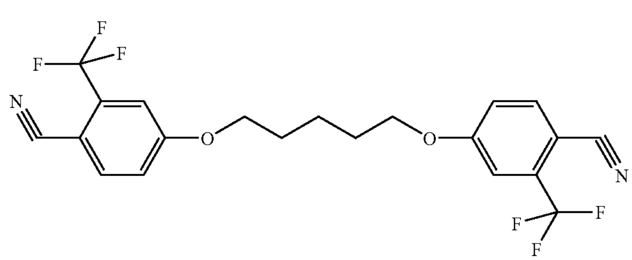 | 128 (a) |

TABLE II-continued

| Example # | Structure | AR Binding IC$_{50}$ (nM) |
|---|---|---|
| 25 | 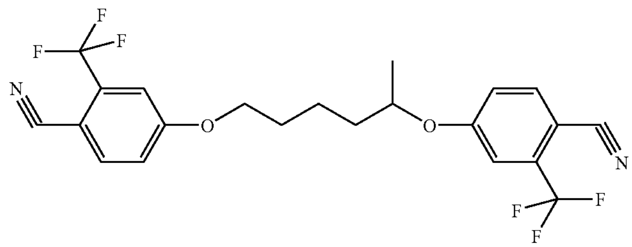 | 159 (a) |
| 26 | 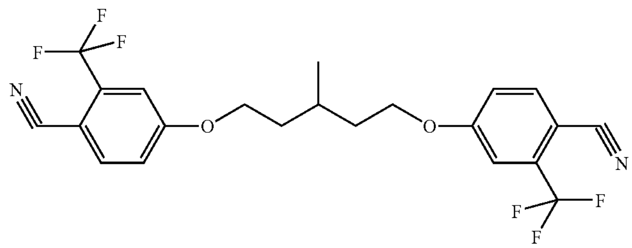 | 156 (a) |
| 27 | 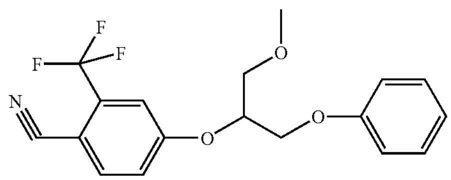 | 5 (a) |
| 28 | 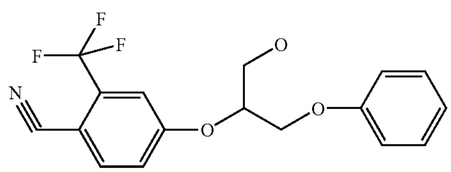 | 81 (a) |
| 29 | 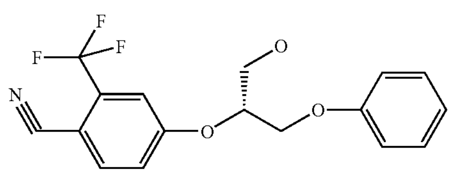 | 44 (a) |
| 30 | 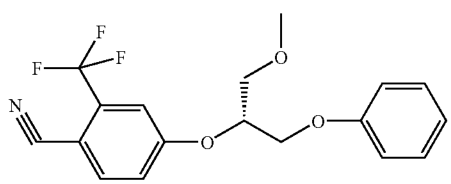 | 30 (n = 6) |
| 31 | | 46 (c) | a—mean of 2 tests
b—mean of 3 tests
c—mean of 4 tests
ND—not determined

Example 33

The compounds ability to antagonize the effects of androgen on the androgen receptor were determined in a whole cell assay as described immediately below.

Experimental Procedure for AR Antagonist Cell Assay

Cell line: MDA-MB453-MMTV clone 54-19. This cell line is a stable transfected cell line with MDA-MB453 cell background (a human breast tumor cell line expressing androgen receptor). A MMTV minimal promoter containing ARE was first cloned in front of a firefly luciferase reporter gene. Then the cascade was cloned into transfection vector pUV120puro. Electroporation method was used for transfecting MDA-MB-453 cell. Puromycin resistant stable cell line was selected.

Cell Culture Media and Reagents:
  Culture medium: DMEM (high glucose, Gibco cat #: 11960-044), 10% FBS, and 1% L-glutamine
  Plating medium: DMEM (phenol red free), 10% charcoal treated HyClone serum, 1% L-glutamine
  Assay medium: DMEM (phenol red free), 1% charcoal treated HyClone serum, 1% L-glutamine, and 1% penicillin/streptomycin
  3X luciferase buffer: 2% beta-mercaptoethanol, 0.6% ATP, 0.0135% luciferine in cell lysis buffer Assay Procedure:
1. Cells are maintained in culture medium, splitting cells when they reach 80-90% confluence
2. To test compounds, 10,000 cells/well are plated to opaque 96 cell culture plate in 100 ul/well plating medium, culture for overnight at 37° C. in cell culture incubator
3. Carefully remove plating medium, then add 80 ul/well of pre-warmed assay medium, add 10 ul/well testing compound (final concentration at) 1000 nM, 200 nM, 40 nM, 8 nM, 1.6 nM, and 0.32 nM), incubate at 37° C. for 30 minutes
4. Add 10 ul/well freshly prepared DHT (final concentration at 100 pM) to each well, incubate at 37° C. for 17 hr (overnight)
5. Add 50 ul/well 3X luciferase buffer, incubate at room temperature for 5 minutes, then count on Luminometer The fold induction over background by 100 pM DHT in the absence of testing compounds is standardized as 100% and experimental result is expressed as percentage of inhibition by testing compounds.

The results are described below in Table III. The results are reported as the mean of multiple tests as described below (the numbers of tests are indicated in the footnote). N.D. denotes that the compound was not tested.

TABLE III

| Example # | Structure | AR Cell $IC_{50}$ (nM) |
|---|---|---|
| 1 | 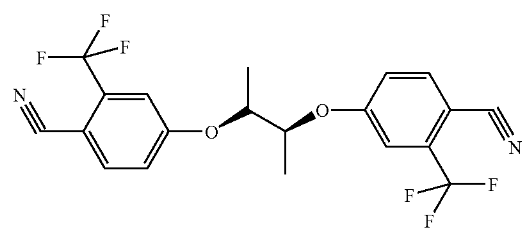 | 531 (a) |
| 2 | 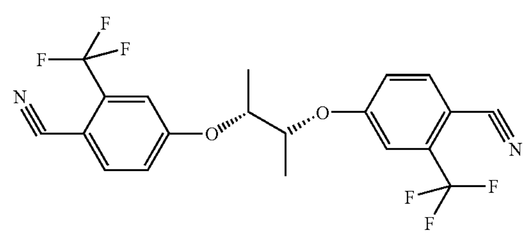 | 67 (a) |
| 3 | 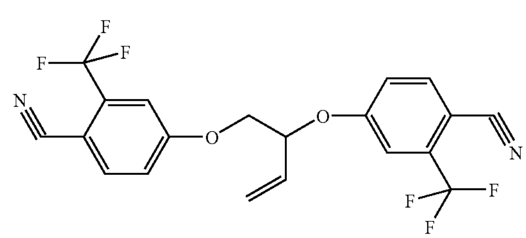 | 457 (a) |

TABLE III-continued

| Example # | Structure | AR Cell IC$_{50}$ (nM) |
|---|---|---|
| 4 | 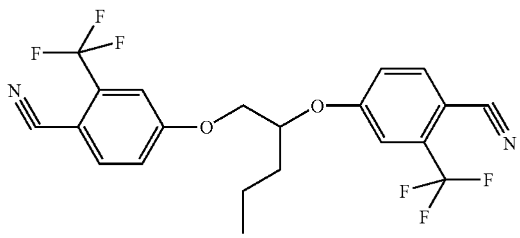 | >1000 (c) |
| 5 | 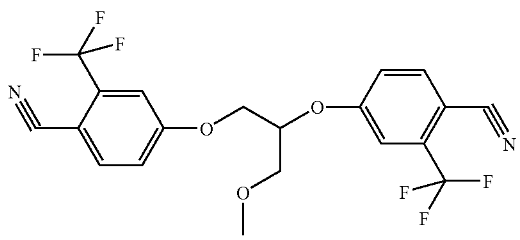 | 187 (a) |
| 6 | 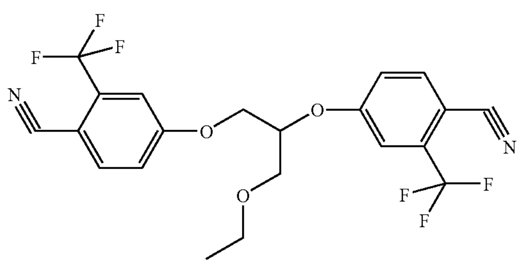 | >1000 (a) |
| 7 | 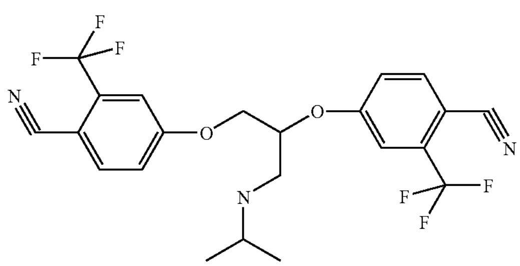 | >1000 (a) |
| 8 | 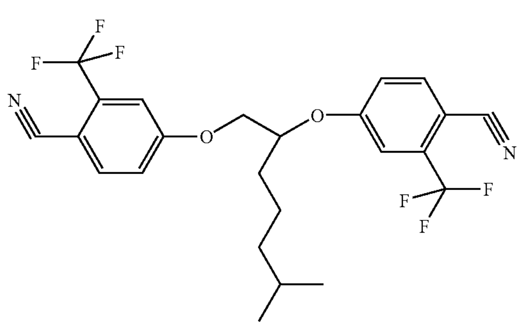 | >1000 (a) |

TABLE III-continued

| Example # | Structure | AR Cell IC$_{50}$ (nM) |
|---|---|---|
| 9 | 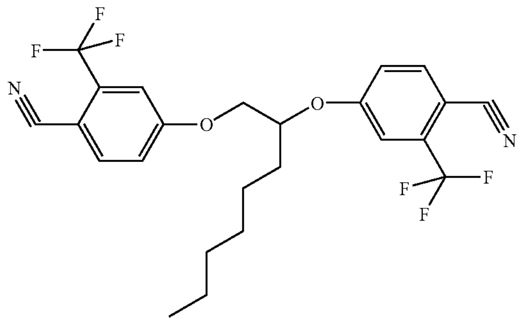 | 531 (a) |
| 10 | 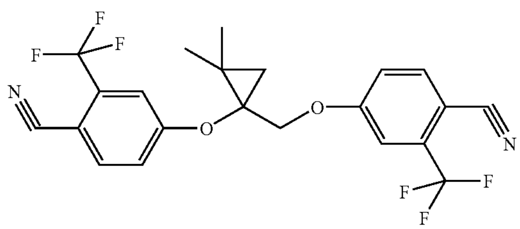 | 447 (a) |
| 11 | 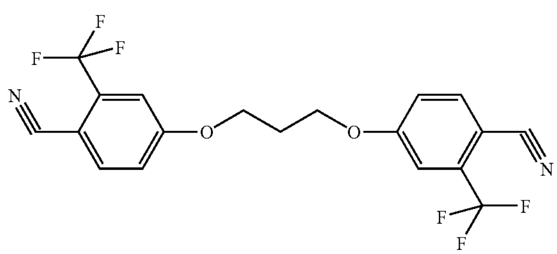 | >1000 (c) |
| 12 | 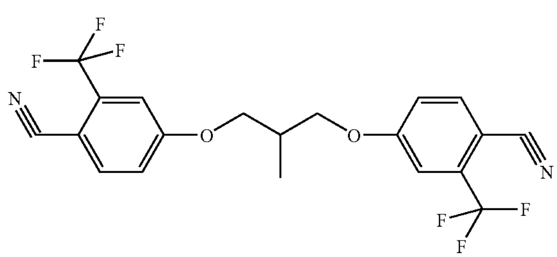 | >1000 (a) |
| 13 | 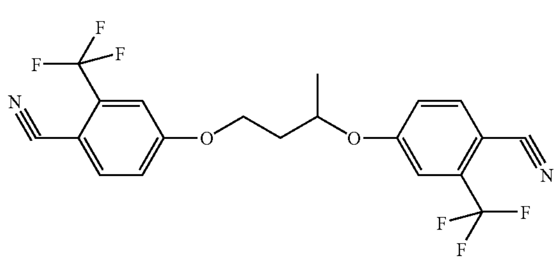 | 100 (c) |

TABLE III-continued

| Example # | Structure | AR Cell IC$_{50}$ (nM) |
|---|---|---|
| 14 | 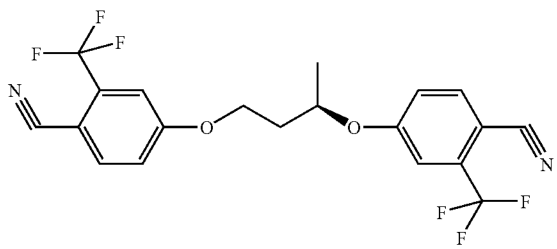 | 905 (a) |
| 15 | 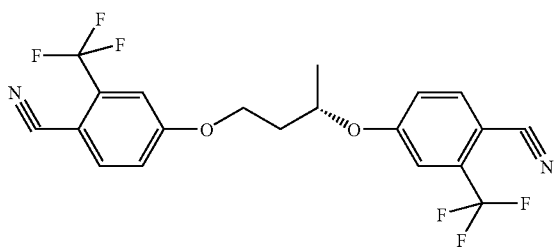 | 257 (a) |
| 16 | 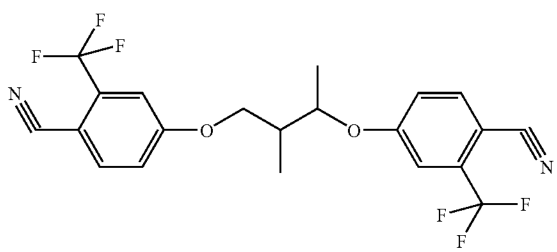 | ND |
| 17 | 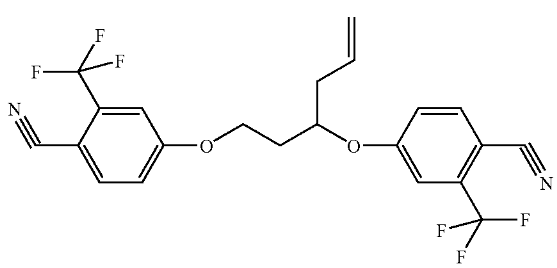 | >1000 (a) |
| 18 | 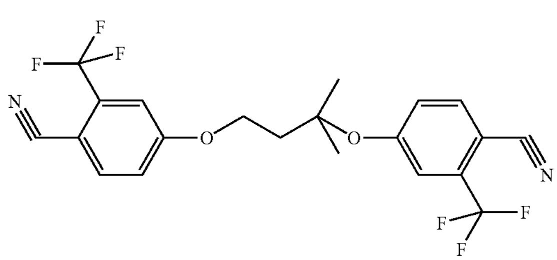 | >1000 (a) |
| 19 | 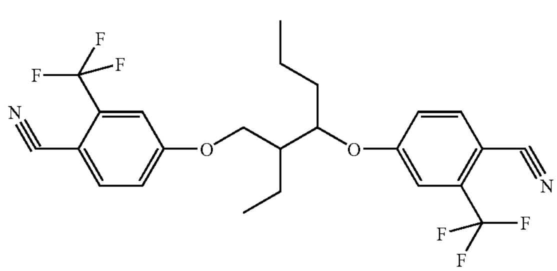 | >1000 (a) |

TABLE III-continued

| Example # | Structure | AR Cell IC$_{50}$ (nM) |
|---|---|---|
| 20 | 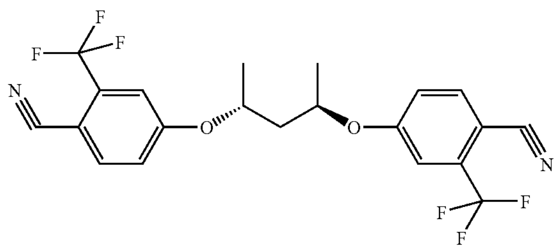 | 159 (a) |
| 21 | 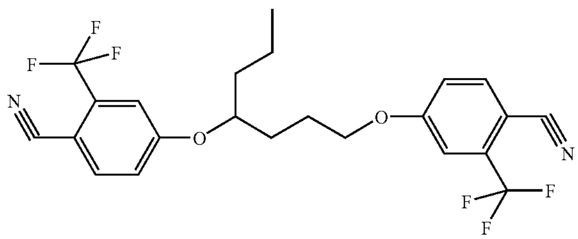 | >1000 (a) |
| 22 | 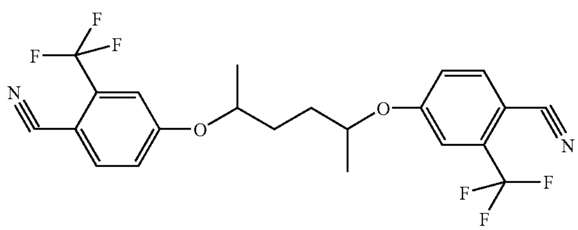 | 322 (a) |
| 23 | 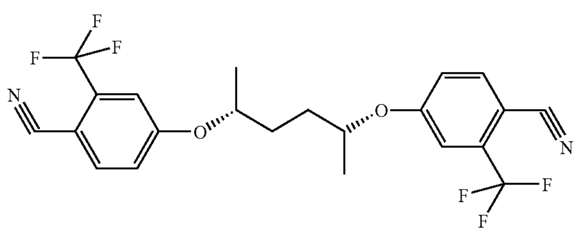 | 202 (a) |
| 24 | 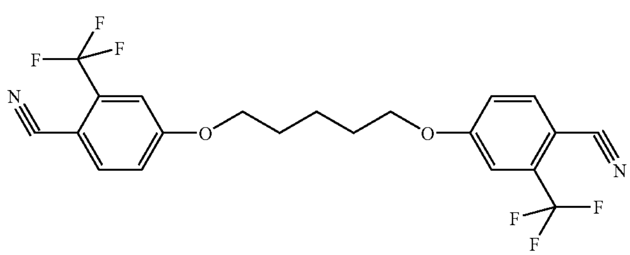 | 64 (a) |
| 25 | 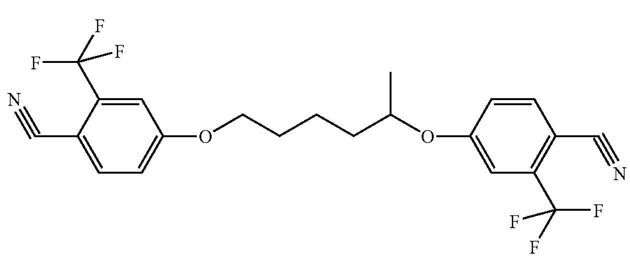 | >1000 (a) |

TABLE III-continued

| Example # | Structure | AR Cell IC$_{50}$ (nM) |
|---|---|---|
| 26 | 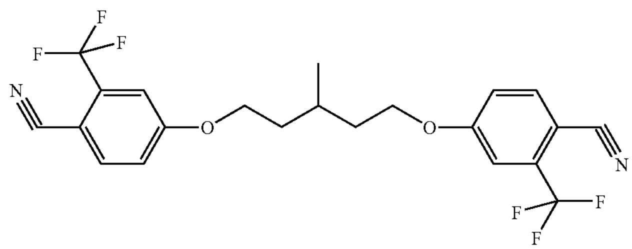 | 212 (a) |
| 27 | 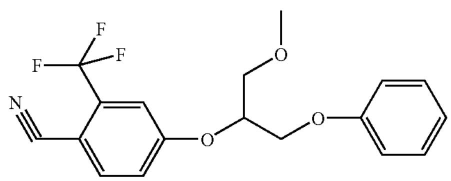 | 19 (a) |
| 28 | 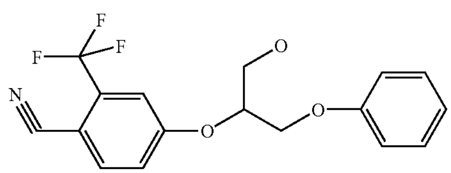 | 69 (a) |
| 29 | 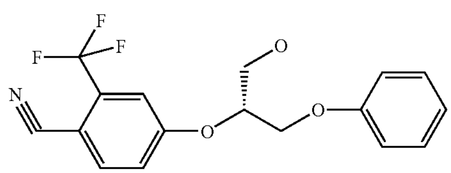 | 117 (a) |
| 30 | 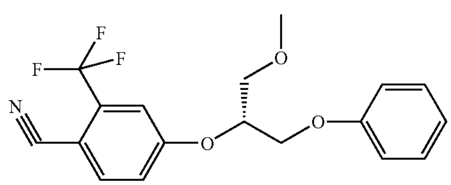 | 40 (N = 6) |
| 31 | | 126 (c) | a—mean of 2 tests
b—mean of 3 tests
c—mean of 4 tests
ND—not determined

Example 34

Animal Model for Inhibition of Sebum Production

Luderschmidt et al describes an animal model for testing whether compounds are capable of modulating sebum secretion. Arch. Derm. Res. 258, 185-191 (1977). This model uses male Syrian hamsters, whose ears contain sebaceous glands. The products of Examples 24, 27 and 28 were screened in this model.

Testing for sebum inhibition was carried out in the following manner. Male Syrian hamsters aged 9 to 10 weeks were introduced into the laboratory environment and acclimated for 2 weeks prior to use in the study. Each group consisted of 5 animals and run in parallel with vehicle and positive controls. Prior to administration, a sufficient quantity each compound was dissolved in 1 mL of a solvent consisting of transcutanol, ethanol, and propylene glycol (20/60/20% v/v) to achieve a final concentration of 0.5 w/v % or 3.0 w/v %.

Animals were dosed topically twice daily, five days a week, for 4 weeks. Each dose consisted of 25 micro liters of vehicle control or drug. The dose was applied to the ventral surfaces of both the right and left ears. All animals were sacrificed approximately 18-24 hours after the final dose. The right ears were collected from each animal and used for sebum analysis.

The ears were prepped for HPLC analysis in the following manner. One 8 mm distal biopsy punch was taken, just above the anatomical "V" mark in the ear to normalize the sample area. The punch was pulled apart. The ventral biopsy surface (the area where the topical dose was directly applied to the sebaceous glands) was retained for testing and the dorsal surface of the biopsy punch was discarded.

Tissue samples were blown with $N_2$ gas and stored at −80° C. under nitrogen until HPLC analysis. In addition to ear samples, an aliquot of each drug and vehicle (at least 250 ul) was also stored at −80° C. for inclusion in the HPLC analysis.

HPLC analysis was carried out on an extract of the tissue sample. Tissue samples were contacted with 3 ml of solvent (a 4:1 admixture of 2,2,4-trimethylpentane and isopropyl alcohol). The mixture was shaken for 15 minutes and stored overnight at room temperature, protected from light. The next morning 1 milliliter of water was added to the sample and shaken for 15 minutes. The sample was then centrifuged at approximately 1500 rpm for 15 minutes. Two ml of the organic phase (top layer) was transferred to a glass vial, dried at 37° C., under nitrogen, for approximately 1 hour, and then lyophilized for approximately 48 hours. The samples were then removed from the lyophilizer and each vial was reconstituted with 600 μl of solvent A (trimethylpentane/tetrahydrofuran (99:1). The samples were then recapped and vortexed for 5 minutes.

200 μl of each sample was then transferred to a pre-labeled 200 μl HPLC vial with 200 μL glass inserts. The HPLC vials were placed in the autosampler tray for the Agilent 1100 series HPLC unit. The Agilent 1100 HPLC system consisted of a thermostated autosampler, a quarternary pump, a column heater, and an A/D interface module. All components were controlled by Agilent ChemStation software. A Waters Spherisorb S3W 4.6×100 mm analytical column was maintained at 30° C. by the Agilent column heater unit. The HPLC autosampler was programmed to maintain the sample temperature at 20 C throughout the run.

10 uL of each sample was injected in triplicate into the column. Two solvents were used for the solvent gradient. Solvent A was an admixture of trimethylpentane and tetrahydrofuran (99:1). Solvent B was ethylacetate. The gradient utilized is described in the table below:

| Time (min) | Solv A (%) | Solv B (%) | Flow (mL/min) |
|---|---|---|---|
| 0 | 99 | 1 | 2 |
| 2 | 96 | 4 | 2 |
| 6 | 60 | 40 | 2 |
| 7 | 5 | 95 | 2 |
| 10 | 5 | 95 | 2 |
| 10.1 | 99 | 1 | 2 |

The Sedex 75 Evaporative Light Scattering Detector (ELSD) was operated at 45° C. with a gain of 5, and $N_2$ pressure maintained at 3.1 bar. Analog signal obtained by the instrument was sent to the Agilent A/D interface module where it was converted to a digital output. The conversion was based on a 10000 mAU/volt set point and the data rate was set at 10 Hz (0.03 min). The resulting digital output was then feed into the Agilent ChemStation software for integration of the peak area.

The results of the HPLC analysis are reported below in Table IV. The results are reported as the reduction in cholesterol ester (CE) and wax ester (WE) production, when compared to the vehicle control. A negative value reflects an increase in sebum, whereas a positive reflects a decrease.

TABLE 12

| Compound | Structure | % Reduction in CE | % Reduction in WE | Sum CE + WE |
|---|---|---|---|---|
| Example 24 0.5 w/v % | 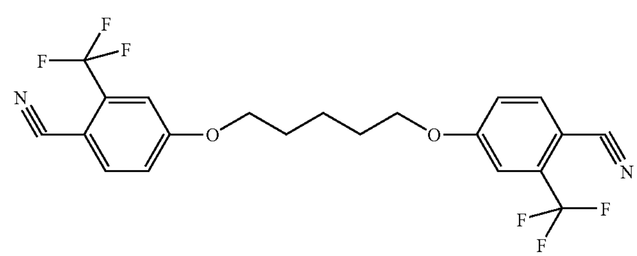 | −33 | −41 | −74 |
| Example 27 3 w/v % | 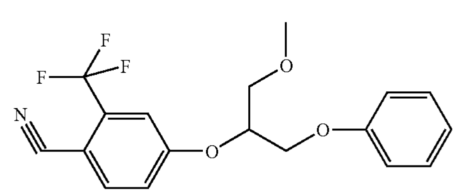 | 63% | 84% | 147 |

TABLE 12-continued

| Compound | Structure | % Reduction in CE | % Reduction in WE | Sum CE + WE |
| --- | --- | --- | --- | --- |
| Example 28 3 w/v % | 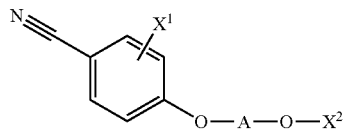 | 11% | 19% | 40 |

What is claimed is:

1. A compound of the formula:

N≡C—⟨phenyl⟩—$X^1$, with O—A—O—$X^2$ or a pharmaceutically acceptable salt, thereof, in which;
a) $X^1$ is represented by trifluoromethyl, and is located at the 3-position of the phenyl ring,
b) A is represented by a linear alkylene group containing from 2 to 10 carbon atoms, in which up to 6 hydrogen atoms may optionally be replaced by a substituent independently selected from the group consisting of:
  i. halogen,
  ii. cyano,
  iii. hydroxy,
  iv. ($C_1$-$C_{12}$)alkyl, optionally substituted,
  v. ($C_2$-$C_{12}$)alkenyl, optionally substituted,
  vi. ($C_2$-$C_{12}$)alkynyl, optionally substituted,
  vii. ($C_3$-$C_{10}$)cycloalkyl, optionally substituted,
  viii. ($C_3$-$C_{10}$) cycloalkyl($C_1$-$C_6$)alkyl, in which the alkyl and cycloalkyl moieties may each be optionally substituted,
  ix. $(CH_2)_n$—$SR^1$,
  x. $(CH_2)_n$—O—$R^1$,
  xi. $(CH_2)_n$—$NR^1R^2$,
  xii. $(CH_2)_n$—$COOR^3$ and,
  xiii. $(CH_2)_n$—$CONR^4$;
c) $X^2$ is represented by ($C_6$-$C_{10}$)aryl, optionally substituted;
d) n, at each occurrence, is independently represented by an integer from 0 to 6;
e) $R^1$ and $R^2$ are each independently represented by a substituent selected from the group consisting of hydrogen and ($C_1$-$C_6$)alkyl, optionally substituted;
f) $R^3$ is represented by a substituent selected from the group consisting of hydrogen, and ($C_1$-$C_6$)alky, optionally substituted, and;
g) $R^4$ is represented by a substituent selected from the group consisting of hydrogen, and ($C_1$-$C_6$)alkyl, optionally substituted.

2. A compound according to claim 1 in which A is represented by ethylene, propylene, butylenes, or pentylene, any of which may be optionally substituted.

3. A compound according to claim 1 in which A is ethylene or propylene and is substituted with at least one substituent represented by $(CH_2)_n$—O—$R^1$ or ($C_1$-$C_6$)alkyl.

4. A compound according to claim 1 selected from the group consisting of:
a. 4,4'-[(2S,3S)-butane-2,3-diylbis(oxy)]bis[2-(trifluoromethyl)benzonitrile]);
b. 4,4'-[(2R,3R)-butane-2,3-diylbis(oxy)]bis[2-(trifluoromethyl)benzonitrile];
c. 4,4'-[but-1-ene-3,4-diylbis(oxy)]bis[2-(trifluoromethyl)benzonitnle];
d. 4,4'-[pentane-1,2-diylbis(oxy)]bis[2-(trifluoromethyl)benzonitrile];
e. 4,4'-[(3-methoxypropane-1,2-diyl)bis(oxy)]bis[2-(trifluoromethyl)benzonitnle];
f. 4,4'-[(3-ethoxypropane-1,2-diyl)bis(oxy)]bis[2-(trifluoromethyl)benzonitrile];
g. 4,4'-[[3-(isopropylamino)propane-1,2-diyl]bis[2-(trifluoromethyl)benzonitrile];
h. 4,4'-[(6-methylhexane-1,2-diyl)bis(oxy)]bis[2-(trifluoromethyl)benzonitrire];
i. 4,4'-[octane-1,2-diylbis(oxy)]bis[2-(trifluoromethyl)benzonitrile];
j. 4-[1-(4-Cyano-3-trifluoromethyl-phenoxymethyl)-2,2-dimethyl-cyclopropoxy]-2-trifluoromethyl-benzonitrile;
k. 4,4'-[Propane-1,3-diylbis(oxy)]bis[2-(trifluoromethyl)benzonitrile];
l. 4,4'-[(2-methylpropane-1,3-diyl)bis(oxy)]bis[2-(trifluoromethyl)benzonitrile];
m. 4,4'-[butane-1,3-diylbis(oxy)]bis[2-(trifluoromethyl)benzonitrile];
n. 4-({(3R)-3-[4-cyano-3-(trifluoromethyl)phenoxy]butyl}oxy)-2-(trifluoromethyl)benzonitrile;
o. 4-({(3S)-3-[4-cyano-3-(trifluoromethyl)phenoxy]butyl}oxy)-2-(trifluoromethyl)benzonitrile;
p. 4-{3-[4-cyano-3-(trifluoromethyl)phenoxy]-1,2-dimethylpropoxy}-2-(trifluoromethyl)benzonitrile;
q. 4,4'-[hex-1-ene-4,6-diylbis(oxy)]bis[2-(trifluoromethyl)benzonitrile];
r. 4,4'-[(3-methylbutane-1,3-diyl)bis(oxy)]bis[2-(trifluoromethyl)benzonitrile];
s. 4-{[3-(4-cyanophenoxy)-2-ethylhexyl]oxy}bis[2-(trifluoromethyl)benzonitrile];
t. 4,4'-[(2S,4S)-pentane-2,4-diyibis(oxy)]bis[2-(trifluoromethyl)benzonitrile];
u. 4,4'-[heptane-1,4-diylbis(oxy)]bis[2-(trifluoromethyl)benzonitrile];
v. 4,4'-[hexane-2,5-diylbis(oxy)]bis[2-(trifluoromethyl)benzonitrile];
w. 4,4'-[(2S,5S)-hexane-2,5-diylbis(oxy)]bis[2-(trifluoromethyl)benzonitrile];
x. 4-({5-[4-cyano-2-(trifluoromethyl)phenoxy]pentyl}oxy)-2(trifluoromethyl)benzonitrile;

y. 4,4'-[hexane-1,5-diylbis(oxy)]bis[2-(trifluoromethyl)benzonitrile];
z. 4,4'-[(3-methylpentane-1,5-diyt)bis(oxy)]bis[2-(trifluoromethyl)benzonitnle];
aa. 4-(1-methoxymethy(-2-phenoxy-ethoxy)-2-trifluoromethyl-benzonitrile;
bb. 4-(1-hydroxymethyl-2-phenoxy-ethoxy)-2-trifluoromethyl-benzonitrile;
cc. (1R)-4-(1-hydroxymethyl-2-phenoxy-ethoxy)-2-trifluoromethyl-benzonitrile;
dd. (1R)-4-(1-methoxymethyl-2-phenoxy-ethoxy)-2-trifluoromethyl-benzonitrile;
ee. (1S)-4-(1-methoxymethyl-2-phenoxy-ethoxy)-2-trifluoromethyl-benzonitrile;
mm. 4.[4-(4-cyano-3-trifluoromethyl-phenoxy)-2-hydroxy-butyloxy]-2-trifluoromethyl-benzonitrile;
nn. 4-[3-(4-cyano-3-trifluoromethyl-phenoxy)-2-cyclohexyl-propyloxy]-2-trifluoromethyl-benzonitrile;
oo. 4-[3-(4-cyano-3-trifluoromethyl-phenoxy)-2-cyclohexyl-propyloxy]-2-trifluoromethyl-benzonitrile;
pp. 4-[3-(4-cyano-3-trifluoromethyl-phenoxy)-2-chloropropyloxy]-2-trifluoromethyl-benzonitrile;
qq. 4-[8-(4-cyano-3-trifluoromethyl-phenoxy)-2-chloro-4-hydroxy-octyloxy]-2-trifluoromethyl-benzonitrile;
rr. 4-[10-(4-cyano-3-trifluoromethyl-phenoxy)-2-methylcyclopentyl-octyloxy]-2-trifluoromethyl-benzonitrile;
ss. 4-[10-(4-cyano-3-trifluoromethyl-phenoxy)-decyloxy]-2-trifluoromethyl-benzonitrile;
tt. 4-[7-(4-cyano-3-trifluoromethyl-phenoxy)-2-cyano-4-methyl-6-hydroxy-heptyloxy]-2-trifluoromethyl-benzonitrile;
uu. 4-(3-(3-hydroxy-4-fluoro-phenoxy)-propoxy)-2-trifluoromethyl-benzonitrile;
vv. 4-(2-cyano-4-dimethylamino-8-phenoxy-octyloxy)-2-trifluoromethyl-benzonitrile;
ww. 4-(2-dimethylamino-2-(4-cyano-phenoxy)-ethyloxy)-2-trifluoromethyl-benzonitrile;
xx. 4-(1-cyclopentyloxymethyl-3-(4-hydroxy-phenoxy)-propoxy)-2-trifluoromethyl-benzonitrile; and
yy. 4-(2-methyl-4-dimethylamino-8-phenoxy-octyloxy)-2-trifluoromethyl-benzonitrile.

5. A compound according to claim 1 in which $X^2$ is phenyl, optionally substituted, with at least one substituent selected from the group consisting of cyano, halogen, and haloalkyl.

6. A compound according to claim 5 in which A is represented by ethylene or propylene.

7. A compound according to claim 5 in which A is ethylene or propylene and is substituted with at least one substituent represented by $(CH_2)_n$—O—$R^1$ or $(C_1$-$C_6)$alkyl.

8. A compound according to claim 1 in which $X^2$ is unsubstituted phenyl.

9. A compound according to claim 8 in which A is represented by ethylene or propylene.

10. A compound according to claim 8 in which A is ethylene or propylene and is substituted with at least one substituent represented by $(CH_2)_n$—O—$R^1$ or $(C_1$-$C_6)$alkyl.

11. A compound according to claim 1 in which A is represented by ethylene or propylene.

12. A compound according to claim 1 in which A is ethylene or propylene and is substituted with at least one substituent represented by $(CH_2)_n$—O—$R^1$ or $(C_1$-$C_6)$alkyl.

13. A compound according to claim 1 in which A is substituted with at least one substituent represented by $(CH_2)_n$—O—$R^1$ or $(C_1$-$C_6)$alkyl.

\* \* \* \* \*